(12) United States Patent
Tsubone et al.

(10) Patent No.: US 10,343,341 B2
(45) Date of Patent: Jul. 9, 2019

(54) THERMAL CAULKING DEVICE

(71) Applicant: SEIDENSHA ELECTRONICS CO., LTD., Arakawa-ku, Tokyo (JP)

(72) Inventors: Shigemasa Tsubone, Tokyo (JP); Noriaki Matsugishi, Tokyo (JP)

(73) Assignee: SEIDENSHA ELECTRONICS CO., LTD., Tokyo (JP)

( * ) Notice: Subject to any disclaimer, the term of this patent is extended or adjusted under 35 U.S.C. 154(b) by 481 days.

(21) Appl. No.: 15/100,185

(22) PCT Filed: Aug. 31, 2015

(86) PCT No.: PCT/JP2015/074765
§ 371 (c)(1),
(2) Date: May 27, 2016

(87) PCT Pub. No.: WO2017/037847
PCT Pub. Date: Mar. 9, 2017

(65) Prior Publication Data
US 2017/0203499 A1    Jul. 20, 2017

(51) Int. Cl.
*B29C 65/32* (2006.01)
*A61M 25/00* (2006.01)
(Continued)

(52) U.S. Cl.
CPC ......... *B29C 65/32* (2013.01); *A61M 25/0009* (2013.01); *B29C 65/18* (2013.01);
(Continued)

(58) Field of Classification Search
CPC ........ B29C 66/92443; B29C 66/91951; B29C 66/91655; B29C 66/91443; B29C 66/861;
(Continued)

(56) References Cited

U.S. PATENT DOCUMENTS 3,946,539 A * 3/1976 Noack ................ B29C 66/0342
53/586
4,521,366 A * 6/1985 Mason ...................... A61J 1/10
264/310
(Continued)

FOREIGN PATENT DOCUMENTS

DE         19537080 A1    4/1997
DE      102012021836 A1    5/2014
(Continued)

OTHER PUBLICATIONS

European Search Report, European Patent Office, Application No. 15866379.9, dated Mar. 22, 2019, 11pages.

*Primary Examiner* — Nahida Sultana
(74) *Attorney, Agent, or Firm* — Greenblum & Bernstein, P.L.C.

(57) ABSTRACT

The present invention provides a thermal caulking device which can quickly heat and cool an object to be caulked with low electrical power. Provided is a thermal caulking device which caulks a portion of a plastic part 7 as an object to be caulked, the thermal caulking device including: a metal tip 3 having a pressing part 3a which presses the object to be caulked and a heating rod 3c which is provided upright at a center part of the pressing part 3a; heating means 10c for heating the heating rod 3c; a cooling pipe 9 which cools the heating rod 3c; cooling fluid supply means 4 for supplying a cooling fluid to the cooling pipe 9; a holder 1 which holds the metal tip 3 and the cooling pipe 9 so that the cooling pipe 9 delivers the cooling fluid toward the heating rod 3c; and control means 6 for controlling the heating means 10c and the cooling fluid supply means 4, wherein the control means 6 heats the pressing part 3a from the heating rod 3c by the heating means 10c, and after the object to be caulked is thermally caulked by the pressing part 3a, supplies the (Continued)

cooling fluid from the cooling fluid supply means 4 to the cooling pipe 9 to cool the pressing part 3*a* from the heating rod 3*c*.

14 Claims, 31 Drawing Sheets

(51) Int. Cl.
*B29C 65/20* (2006.01)
*B29C 65/00* (2006.01)
*H05B 3/06* (2006.01)
*H05B 3/42* (2006.01)
*B29C 65/18* (2006.01)
*B29C 65/60* (2006.01)
*B29C 65/64* (2006.01)
*H05B 6/10* (2006.01)
*H05B 6/14* (2006.01)
*B29L 31/00* (2006.01)
*B29C 35/08* (2006.01)

(52) U.S. Cl.
CPC ............ *B29C 65/20* (2013.01); *B29C 65/601* (2013.01); *B29C 65/606* (2013.01); *B29C 65/64* (2013.01); *B29C 66/0342* (2013.01); *B29C 66/1122* (2013.01); *B29C 66/21* (2013.01); *B29C 66/30321* (2013.01); *B29C 66/30325* (2013.01); *B29C 66/3494* (2013.01); *B29C 66/41* (2013.01); *B29C 66/7392* (2013.01); *B29C 66/742* (2013.01); *B29C 66/8122* (2013.01); *B29C 66/8161* (2013.01); *B29C 66/8167* (2013.01); *B29C 66/81423* (2013.01); *B29C 66/81429* (2013.01); *B29C 66/81431* (2013.01); *B29C 66/81811* (2013.01); *B29C 66/8242* (2013.01); *B29C 66/8322* (2013.01); *B29C 66/83221* (2013.01); *B29C 66/847* (2013.01); *B29C 66/861* (2013.01); *B29C 66/91421* (2013.01); *B29C 66/91443* (2013.01); *B29C 66/91643* (2013.01); *B29C 66/91655* (2013.01); *B29C 66/91951* (2013.01); *B29C 66/92443* (2013.01); *B29C 66/92921* (2013.01); *H05B 3/06* (2013.01); *H05B 3/42* (2013.01); *H05B 6/101* (2013.01); *H05B 6/14* (2013.01); *B29C 66/863* (2013.01); *B29C 66/9672* (2013.01); *B29C 66/9674* (2013.01); *B29C 2035/0811* (2013.01); *B29K 2905/00* (2013.01); *B29K 2995/0008* (2013.01); *B29L 2031/7542* (2013.01); *B29L 2031/7543* (2013.01); *B29L 2031/7546* (2013.01)

(58) Field of Classification Search
CPC ............ B29C 66/847; B29C 66/83221; B29C 66/8322; B29C 66/8242
See application file for complete search history.

(56) References Cited

U.S. PATENT DOCUMENTS

| | | | |
|---|---|---|---|
| 4,792,373 A | * | 12/1988 | Hsei .................. B29C 66/133 156/497 |
| 6,212,861 B1 | * | 4/2001 | Tsuruta ................ B29C 65/18 53/374.6 |
| 6,298,533 B1 | * | 10/2001 | Nishimura ........ B29C 66/81821 29/243.5 |
| 2002/0017744 A1 | | 2/2002 | Lochner et al. |
| 2010/0193125 A1 | * | 8/2010 | Thomasset ............ B29C 53/20 156/296 |

FOREIGN PATENT DOCUMENTS

| | | |
|---|---|---|
| EP | 1180405 A2 | 2/2002 |
| JP | S53-040883 A | 4/1978 |
| JP | 57-195616 A | 12/1982 |
| JP | 11-056753 A | 3/1999 |
| JP | 2004229976 A | 8/2004 |
| JP | 2005001268 A | 1/2005 |
| WO | 2009050888 A | 4/2009 |

\* cited by examiner

FIG. 11

| | ITEM (PARAMETER) | WELDING CONDITION | | | | |
|---|---|---|---|---|---|---|
| | | CONDITION 1 | CONDITION 2 | CONDITION 3 | CONDITION 4 | CONDITION 5 |
| 1 | X (BOSS OUTER DIAMETER) | X1 | X1 | X1 | X1 | X1 |
| 2 | Y (BOSS CAULKING AMOUNT) | Y1 | Y1 | Y1 | Y1 | Y1 |
| 3 | Z (BOSS MATERIAL) | Z1 | Z1 | Z1 | Z1 | Z1 |
| 4 | SCORE | 98 | 95 | 92 | 88 | 86 |
| 5 | K (PRESSING PART SHAPE) | CONCAVE-1 | CONCAVE-1 | CONCAVE-2 | CONCAVE-2 | CONCAVE-3 |
| 6 | D (WALL PART OUTER DIAMETER) | D1 | D1 | D2 | D2 | D3 |
| 7 | N (WALL PART THICKNESS) | N1 | N1 | N1 | N1 | N1 |
| 8 | d (HEATING ROD DIAMETER) | d1 | d2 | d1 | d2 | d1 |
| 9 | H (HEATING ROD HEIGHT) | H1 | H2 | H1 | H2 | H1 |
| 10 | F (PRESSING FORCE) | F1 | F2 | F3 | F4 | F5 |
| 11 | I (HIGH-FREQUENCY CURRENT) | I1 | I2 | I3 | I4 | I5 |
| 12 | Q (COOLING FLUID FLOW RATE) | Q1 | Q2 | Q3 | Q4 | Q5 |
| 13 | T (METAL TIP TEMPERATURE) | T1 | T1 | T1 | T1 | T1 |
| 14 | t₁ (PRESSING/CURRENT APPLICATION START TIME) | t11 | t12 | t13 | t14 | t15 |
| 15 | t₂ (CURRENT APPLICATION END/COOLING START TIME) | t21 | t22 | t23 | t24 | t25 |
| 16 | t₃ (COOLING END TIME) | t31 | t32 | t33 | t34 | t35 |
| 17 | t₄ (PRESSING END TIME) | t41 | t42 | t43 | t44 | t45 |

FIG. 23 PRIORT ART
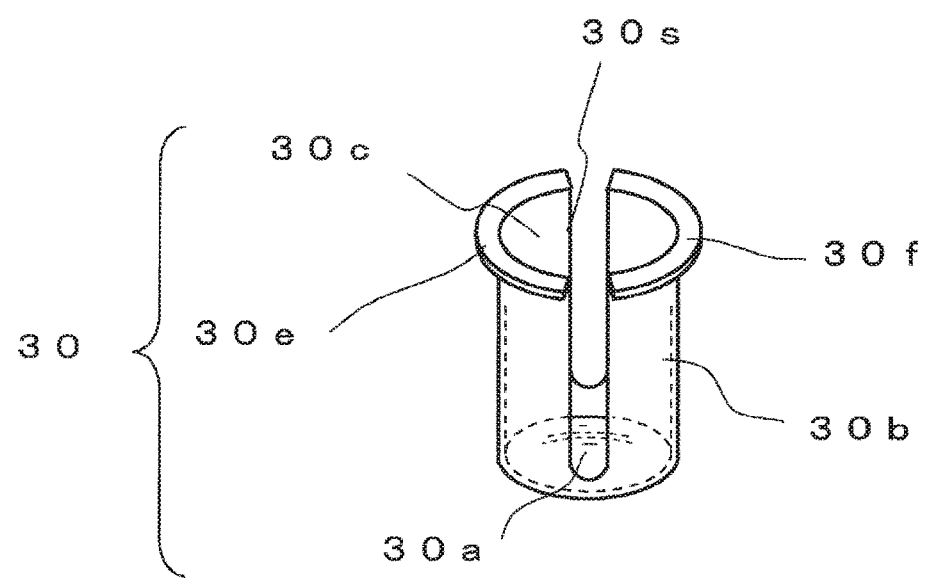

FIG. 24A PRIORT ART
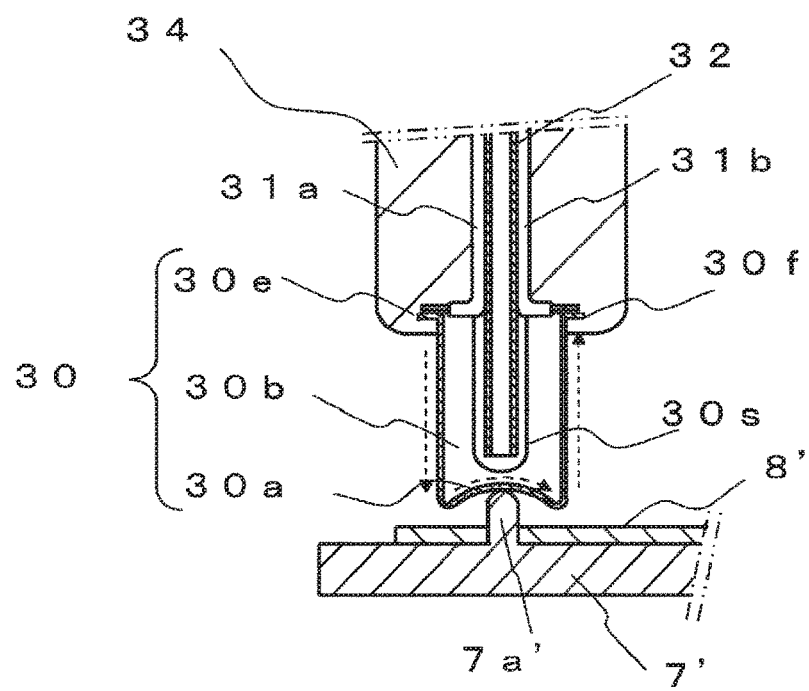
FIG. 24B PRIORT ART
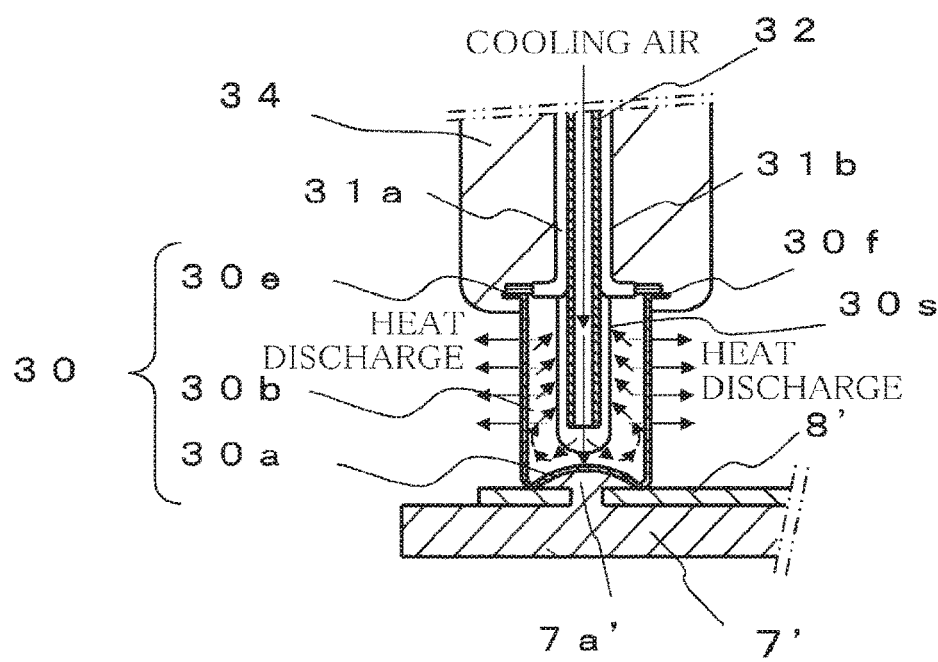

FIG. 28A  PRIOR ART
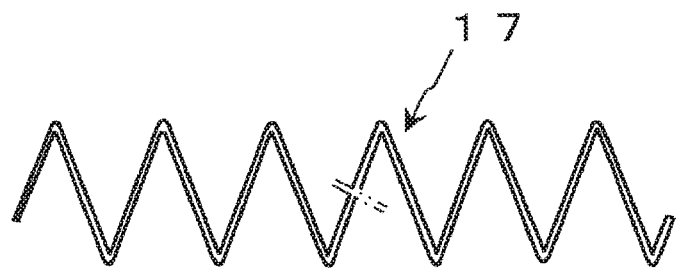
FIG. 28B  PRIOR ART
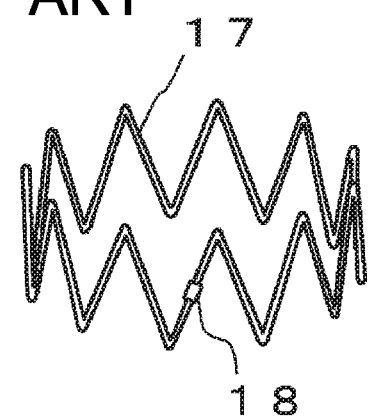
FIG. 28C  PRIOR ART
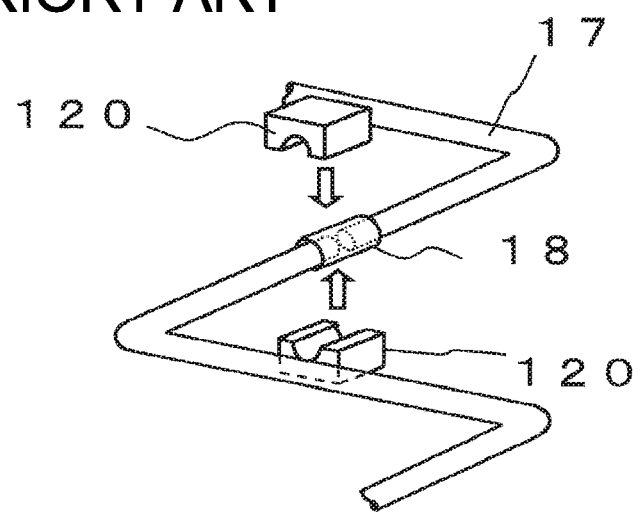

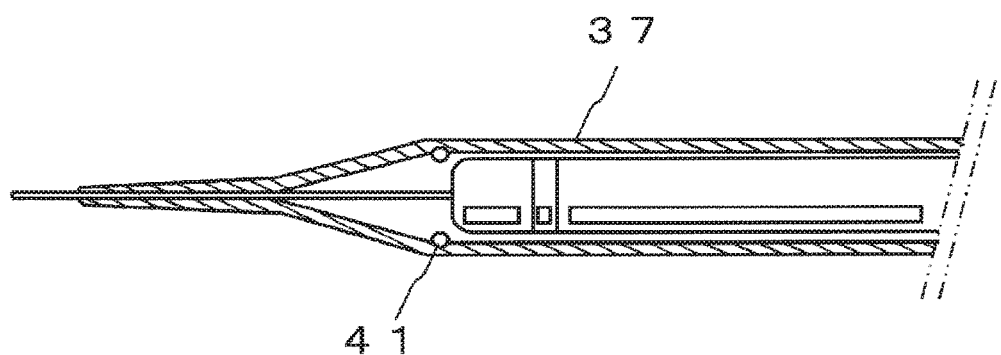
FIG. 29 PRIORT ART

THERMAL CAULKING DEVICE

TECHNICAL FIELD

The present disclosure relates to a thermal caulking device, and more particularly to a thermal caulking device which caulks a plastic part using a metal tip heated by high-frequency induction heating or electrical heating.

BACKGROUND ART

In general, a method of caulking a boss is widely practiced as a method for fixing a metal plate etc. to a plastic part. In this method, a columnar protrusion (hereinafter referred to as a "boss") of a proper size is provided at a predetermined position in a plastic part, while a hole into which the boss can be inserted is bored in a metal plate or a plastic plate to be fixed to the plastic part. After the two are fitted together, the boss protruding from the hole is subjected to ultrasonic vibration or heat to melt and deform and thereby caulk the boss.

The method using heat is today widely used because of its advantages over the method using ultrasonic vibration: (1) beautiful finish, (2) no influence of vibration on the part, (3) simple principle, hence easy maintenance, and (4) relatively low device cost compared with ultrasonic vibration. A heater used for caulking a boss is molded of a nichrome plate or formed by cutting a metal having a relatively high electrical resistance, and the heater uses Joule heat which is generated as a high current is passed therethrough.

One example of conventional thermal caulking devices is shown in FIG. 22. For the thermal caulking device shown in FIG. 22, a perforated metal plate 8' is fitted with a boss 7a' which is a columnar protrusion of a plastic part 7'. This thermal caulking device thermally caulks the boss 7a' by pressing a metal tip 30, heated to or above the softening temperature of the plastic part 7', against the leading end of the boss 7a'.

As shown in FIG. 22, lead wires 31a, 31b are electrically connected by welding or screw fixation to flanges 30e, 30f, respectively, of the metal tip 30 which serves as a caulking heater. In a cavity 30c of the metal tip 30, a plastic cooling pipe 32, which delivers cooling air cooled to or below normal temperature, is disposed so that the opening end of the cooling pipe 32 is located near a pressing part 30a. The metal tip 30, the lead wires 31a, 31b, and the cooling pipe 32 are molded, for example, with epoxy resin 34, so as to retain their respective desired positions.

FIG. 23 is an external perspective view of the metal tip 30 as a single part. The metal tip 30 shown in FIG. 23 has the pressing part 30a which has an upwardly convex spherical surface, and a cylindrical wall part 30b rises from around the pressing part 30a, forming the cavity 30c inside the metal tip 30. The wall part 30b is divided by slits 30s into left and right portions, and the flanges 30e, 30f are formed at the upper end of the wall part 30b.

In FIG. 22, the pressing part 30a of the metal tip 30 is depicted at a position above and at a distance from the boss 7a'. When thermal caulking work is performed, a current flows from the lead wires 31a, 31b to the metal tip 30, and the metal tip 30 is heated by Joule heat. Upon reaching a predetermined temperature, the metal tip 30 is lowered as indicated by the arrow Y to bring the pressing part 30a into contact with the leading end of the boss 7a'. Then, the leading end of the boss 7a' is softened and melted by the heat of the metal tip 30. Thereafter, the application of a current to the lead wires 31a, 31b, is stopped, and cooling air is sprayed from the cooling pipe 32 to the pressing part 30a of the metal tip. The cooling air flows through the slits 30s to the outside. The metal tip 30 and the leading end of the boss 7a' are cooled to a temperature equal to or lower than the softening point of plastic to solidify the leading end of the boss 7a'. Then, the metal tip 30 is raised again, which completes the caulking work.

FIG. 24A and FIG. 24B are cross-sectional view showing a state at the start of thermal caulking work and a state at the end of the thermal caulking work. FIG. 24A shows a stage in which a current is applied from the lead wire 31a to the lead wire 31b to heat the metal tip 30, and the pressing part 30a is pressed against the leading end of the boss 7a' to melt and deform the boss 7a'. Specifically, in FIG. 24A, electrical power is supplied from a power source (not shown) to the lead wire 32a, and a current flows from the lead wire 31a to the flange 30e, the wall part 30b, the pressing part 30a, the wall part 30b, and the flange 30f of the metal tip 30, and the lead wire 31b. Thus, the flange 30e, the wall part 30b, the pressing part 30a, the wall part 30b, and the flange 30f are heated in this order according to the flow of the current. When the pressing part 30a reaches a temperature exceeding the softening point of plastic, deformation of the leading end of the boss 7a', i.e., caulking work starts. By being pressed with the pressing part 30a, the leading end of the boss 7a' assumes a predetermined shape.

FIG. 24B shows a state in which, after the leading end of the boss 7a' has been melted and deformed, the application of a current from the lead wire 31a to the lead wire 31b is stopped, and coaling air is sprayed from cooling air delivery means (not shown) through the cooling pipe 32 to the pressing part 30a inside the cavity 30c to discharge the heat of the metal tip 30 and the melted boss 7a' through the slits 30s and thereby cool the metal tip 30 and the boss 7a'. The flow of the cooling air inside the cavity 30c of the metal tip 30 is indicated by the arrows in FIG. 24B. The cooling air collides with the pressing part 30a inside the cavity 30c, rises along the wall part 30b, and flows through the slits 30s to the outside of the metal tip 30. That is, the heat of the metal tip 30 and the melted boss 7a' is discharged through the slits 30s. Thus, the boss 7a' of the plastic part 7', which is a molded part, is melted, deformed, cooled, and solidified, so that the perforated metal plate 8 is fixed to the plastic part 7' (e.g., see Patent Document 1).

FIG. 25 is a schematic cross-sectional view of another conventional plastic part thermal caulking device which uses high-frequency induction heating means as metal tip heating means. In the thermal caulking device shown in FIG. 25, a plurality of metal tips 40, each having a cavity 60 through which a cooling fluid is circulated, are respectively attached under cooling pipes 70, and an induction heating coil 51 is wound on the outer periphery of each metal tip 40. A high-frequency induction power source 50 is used to pass a high-frequency current through the coil 51 and generate an induced current in the metal tip 40 to thereby heat the metal tip 40. Then, a pressing part 45 of the headed metal tip 40 is pressed against the leading end of the boss 7a' to melt and deform the leading end of the boss 7a'. After the leading end of the boss 7a' has been melted and deformed, the application of a high-frequency current to the coil 51 is stopped, and a cooling fluid, such as cooling air, is sprayed from the cooling pipe 70 inside the cavity 60 of the metal tip 40 in the direction toward the pressing part 45, to cool the metal tip 40 and the heated and melted boss 7a'. Thus, the boss 7a' of the plastic part 7', which is a molded part, is melted, deformed, cooled, and solidified, so that the perforated metal plate (object to be fixed) 8' is fixed to the plastic part 7'.

Since high-frequency induction heating can instantly heat the metal tip 40, it has an advantage over electrical heating in that the caulking step takes a shorter time (e.g., see Patent Document 2).

Thermal caulking of plastic parts is used not only for caulking bosses and shaft parts of about several millimeters in diameter, such as thermally caulking the rotation shaft of plastic scissors of daily use, but also for thermally caulking smaller plastic parts. For example, in the case of a forceps-type electrical treatment tool shown in FIG. 26, a first forceps piece 12b and a second forceps piece 14b are incorporated into a support 67 mounted at the leading end of a catheter tube 47 which can be inserted into the body, and the first forceps piece 12b and the second forceps piece 14b are supported on a plastic support shaft 80. The support shaft 80 is thermally caulked after the support 67, the first forceps piece 12b, and the second forceps piece 14b are passed therethrough, and thus the first forceps piece 12b and the second forceps piece 14b are assembled so as to be able to open and close (e.g., see Patent Document 3).

FIG. 27 is a schematic view showing a step in which heated rod-like metal tips 110 are pressed respectively against both ends of the support shaft 80 of the support 67 mounted at the leading end of the catheter tube 47 to thermally caulk the support shaft 80. The catheter tube 47 is intended to be inserted into the body, such as a blood vessel, and the support 67 as well as the support shaft 80 counted at the leading end of the catheter tube 47 are also small parts. During operation, the first forceps piece 12b and the second forceps piece 14b at the leading end of the catheter tube 47 inserted into the body are required to open and close as intended by a surgeon (doctor). It is undesirable that, the first forceps piece 12b and the second forceps piece 14b do not move smoothly due to too tight caulking, or that the first forceps piece 12b and the second forceps piece 14b come off due to too loose caulking.

Other than the above example, thermal caulking of a stent which is put inside the body by being mounted at the leading end of a balloon catheter, and thermal caulking of a plastic part at the leading end of an endoscope are also known as examples of thermal caulking of catheter-related plastic parts.

FIG. 28A shows an extended state of a stent 17 which is put inside the body by being mounted at the leading end of a balloon catheter. FIG. 28B shows a state in which the stent 17 shown in FIG. 28A is formed into a ring shape and a caulking ring 18 is put thereon. FIG. 28C is a schematic view showing a step in which the caulking ring 18 shown in FIG. 28B is pressed from both sides in the vertical direction with a pair of heated metal tips 120 to thermally caulk the caulking ring 18 (e.g., see Parent Document 4), FIG. 29 shows an endoscope attachment of which a fixing member 41 is fixed by press-fitting and thermal caulking inside a tube 37 at a leading end part of an endoscope (e.g., see Patent Document 5).

Thus, for thermal caulking of small plastic parts, especially medical plastic parts, it is required that the thermal caulking device itself strictly manages heating and pressing conditions of the metal tip and performs thermal caulking stably and precisely under the required best heating and pressing conditions.

PRIOR ART DOCUMENT

Patent Document

Patent Document 1: Japanese Patent Laid-Open No. 2005-1268
Patent Document 2: Japanese Patent Laid-Open No. S57-195616
Patent Document 3: Japanese Patent Laid-Open No. 2004-229976
Patent Document 4: International Publication No. WO 2009-050888
Patent Document 5: Japanese Patent Laid-Open No. H11-56753

SUMMARY OF THE INVENTION

Problems to be Solved by the Invention

The conventional example shown in FIG. 22 which involves electrical heating has the following problems. (1) Since the electrical resistance of the heater (metal tip 30) is low (0.5 to 0.1Ω), a thick electrical wire is required for passing a high current of 20 A to 50 A. Moreover, a transformer for high current is required, so that the size of the power source becomes larger. (2) While it is possible to increase the resistance value by thinning the material of the heater, the metal tip should have a plate thickness of at least 0.2 mm to 0.5 mm, for otherwise the mechanical strength would become insufficient. (3) The heater is required to be heated only at the center part with which the boss first comes into contact. However, the structure as shown in FIG. 22 causes unnecessary parts to be heated as well, which was wastefully consumes electrical power as well as requires time for heating before caulking work and time for cooling after caulking work. (4) In the case of the conventional example shown in FIG. 22, the metal tip 30 cannot be replaced alone when the metal tip 30, which is the heater, or the lead wires 31a, 31b are damaged. (5) A current flows from the lead wire 31a to the lead wire 31b, and the metal tip 30 generates heat along the direction in which the current flows. Since the metal tip 30 is provided with the slits 30s for discharging heat, a temperature difference occurs between both sides of the metal tip 30 across the slits 30s. It is unfavorable that a temperature difference in the pressing part 30a of the metal tip results in uneven heating and melting of the boss 7a' and thus in an uneven caulking force. If the center of the boss 7a' cools and solidifies before the surrounding area, the caulking force cannot be expected to increase during solidification of the center part of the boss 7a'.

The conventional plastic part thermal caulking device shown in FIG. 25 which uses high-frequency induction heating has the following disadvantages. (1) The thickness of the metal tip 40 is large, and the heat capacity of the metal tip 40 is large. Even if the metal tip 40 is reduced in thickness to reduce the heat capacity, since the coil 51 is wound on the outer side of the metal tip 40, a high-output power source for high-frequency induction heating is required due to the large diameter of the coil 51. In addition, heating takes time. (2) If the diameter of a boss is larger, the outer diameter of the metal tip 40 needs to be increased. Then, the outer diameter of the coil 51 is also increased. If the outer diameter of the metal tip 40 varies according to the outer diameter of the boss, the coil 51 needs to be replaced with one corresponding to the outer shape of the metal tip 40. (3) The space occupied by the coil 51 interferes with a caulking worker and limits the work space. The coil 51 interferes with replacement of the metal tip 40.

For the caulking devices described with FIG. 26 to FIG. 29 which are intended for catheter-related plastic parts, small plastic parts at the leading end part of an endoscope, etc., there is a demand for a small and light thermal caulking device of which the metal tip has a small heat capacity and which allows detailed setting of heating and pressing conditions.

The present invention has been devised to solve such problems, and an object of the invention is to provide a thermal caulking device which can quickly heat and cool an object to be caulked with low electrical power. More specifically, objects of the present invention as embodiments thereof are as follows:

(1) To make it possible to sufficiently caulk a thermoplastic resin boss in a short time using a low-output device;

(2) To provide a plastic part thermal caulking device which is highly responsive to heating and cooling;

(3) To increase the caulking force by heating and melting especially the center part of a boss to the maximum temperature so that the boss is cooled and solidified from the periphery toward the center part;

3) To use the same metal tip for thermally caulking bosses of different diameters, even when the outer diameter of the boss is larger or smaller, by heating the boss from the center toward the outer periphery and varying the length of the heating time so as to produce a required amount of heat with the same metal tip;

(5) To allow the metal tip to be easily attached/removed or replaced alone;

(6) To provide a small and light thermal caulking device; and (7) To provide a plastic part thermal caulking device, especially of a high-frequency induction heating type, which has a high-frequency induction heating coil provided on the inside, not the outside, of the metal tip so as not to interface with a caulking worker.

Means for Solving the Problems

To achieve the above objects, a thermal caulking device according to the present invention is a thermal caulking device which caulks a portion of a plastic part as an object to be caulked, the thermal caulking device including: a metal tip having a pressing part which presses the object to be caulked, a heating rod provided upright in a center part of the pressing part, and a wall part provided upright on the outer periphery of the pressing part; heating means for heating the heating rod; a cooling pipe which cools the heating rod; cooling fluid supply means for supplying a cooling fluid to the cooling pipe; a holder which holds the metal tip and the cooling pipe so that the cooling pipe delivers the cooling fluid toward the heating rod; and control means for controlling the heating means and the cooling fluid supply means, wherein the control means heats the pressing part from the heating rod by the heating means, and after the object to be caulked is thermally caulked by the pressing part, supplies the cooling fluid from the cooling fluid supply means to the cooling pipe to cool the pressing part from the heating rod.

Advantageous Effects of the Invention

According to the present invention adopting the above means, it is possible to quickly heat and cool an object to be caulked with low electrical power. Specifically, the objects listed above are achieved in the embodiments of the present invention. That is, the following objects are achieved: (1) To make it possible to sufficiently caulk a thermoplastic resin boss using a low-output device; (2) To provide a plastic part thermal caulking device which is highly responsive to heating and cooling; (3) To increase the caulking force by heating and melting especially the center part of a boss to the maximum temperature so that the boss is cooled and solidified from the periphery toward the center part; (4) To use the same metal tip for thermally caulking bosses of different diameters, even when the outer diameter of the boss is larger or smaller, by heating the boss from the center toward the outer periphery and varying the length of the heating time so as to produce a required amount of heat with the same metal tip; (5) To allow the metal tip to be easily attached/removed or replaced alone; (6) To provide a small and light thermal caulking device; and (7) To provide a plastic part thermal caulking device, especially of a high-frequency induction heating type, which has a high-frequency induction heating coil provided on the inside, not the outside, of the metal tip so as not to interfere with a caulking worker.

Moreover, the thermal caulking device of the present invention has the following effects: (1) The thermal efficiency is high, since the heat from the heated metal rod is transferred to only near the part in contact with the boss; (2) The cooling time is short, since the wall part of the metal tip is not directly heated; (3) A thin electrical wire having a cross-sectional area of about 1 $mm^2$ suffices, since a current passed through the high-frequency induction heating coil is of 2 A to 5 A; (4) The power source is small and light, since only electronic circuits and electronic parts generating high frequency are required and no large transformer is required; and (5) The metal tip is easy to replace when the metal tip gets dirty or damaged.

BRIEF DESCRIPTION OF THE DRAWINGS

FIG. 11 is a view showing examples of detailed thermal caulking conditions stored in a memory of the plastic part thermal caulking device according to the second embodiment of the present invention.

FIG. 23 is an external perspective view of a metal tip of the first conventional plastic part thermal caulking device.

FIG. 24A is a cross-sectional view of the major part showing a state of the first conventional plastic part thermal caulking device at the start of thermal caulking.

FIG. 24B is a cross-sectional view of the major part showing a state of the first conventional plastic part thermal caulking device during heat discharge after thermal caulking.

FIG. 28A is a view showing a state before caulking of a stent which is a conventional plastic part to be thermally caulked.

FIG. 28B is a view showing a preparatory state before caulking of the stent which is a conventional plastic part to be thermally caulked.

FIG. 28C is a view showing a state immediately before the start of thermal caulking in a caulking step of the stent which is a conventional plastic part to be thermally caulked.

FIG. 29 is a view showing a state in which a plastic part at a leading end part of a conventional endoscope has been thermally caulked.

MODE FOR CARRYING OUT THE INVENTION

First Embodiment

Figure 1:
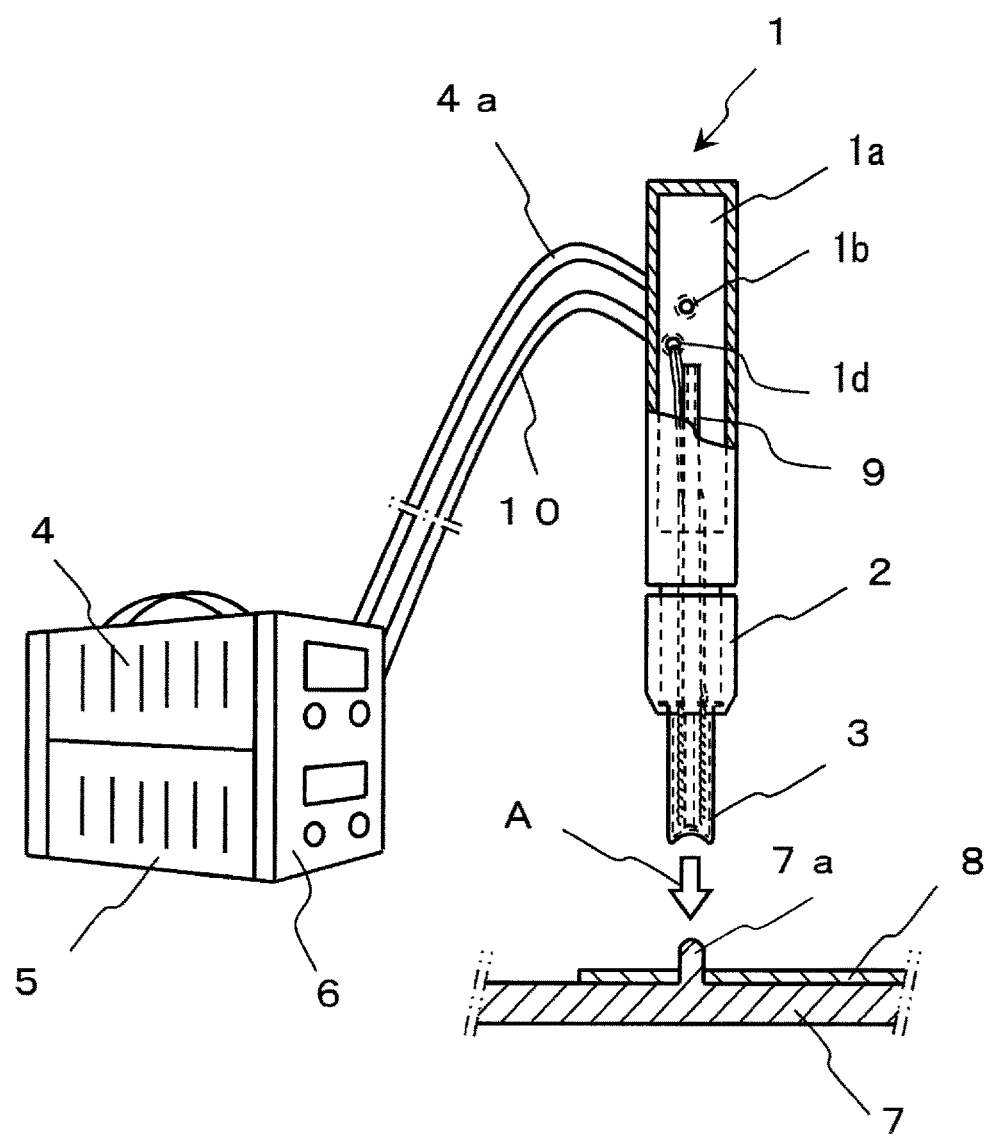
FIG. 1 is an overall configurational view showing a plastic part thermal caulking device according to a first embodiment of the present invention.

FIG. 1 is an overall configurational view showing a plastic part thermal caulking device according to a first embodiment of the present invention. As shown in FIG. 1, the thermal caulking device is provided with a holder cap 2 at the leading end of a hollow rod-like holder 1, the holder 1 and the holder cap 2 holding a metal tip 3. The holder 1 and the holder cap 2 are made of an insulating material, such as plastic, and grasped by a worker or held by a robot or pressing operation means of other production machines. This thermal caulking device can perform thermal caulking operation of integrating a metal plate 8 etc., which is laid on a plastic part 7 and penetrated by a boss 7a, by pressing a pressing part of the heated metal tip 3 against the boss 7a of the plastic part 7.

In FIG. 1, a cooling pipe 9, which will be described in detail later, is disposed inside the holder 1, and the holder 1 has a cooling function of forcibly cooling the metal tip 3 after thermal caulking. For this purpose, the inside of the holder 1 is left as a cavity 1a. A hole 1b is formed in the side surface of the holder 1, and the hole 1b communicates with the inside of a hose 4a of which one end is connected to the side surface of the holder 1. The other end of the hose 4a is connected to a cooling fluid supply machine 4. Another hole 1d is formed in the side surface of the holder 1, and a pair of lead wires 10a, 10b, bundled into one lead wire bundle 10, is passed through the hole 1d. The lead wires 10a, 10b are connected to a heating power source 5 through the hole 1d in the side surface of the holder 1. The cooling fluid supply machine 4 and the heating power source 5 are integrally assembled and form a control unit along with a controller 6. While this will be described later in detail, to enable thermal caulking work, the controller 6 is provided with a control circuit which controls thermal caulking work, a memory which stores various control conditions and stores optimal thermal caulking conditions according to predetermined thermal caulking work, and a thermal caulking condition storage/readout part which stores thermal caulking conditions in the memory and reads out the thermal caulking conditions therefrom.

Figure 2:
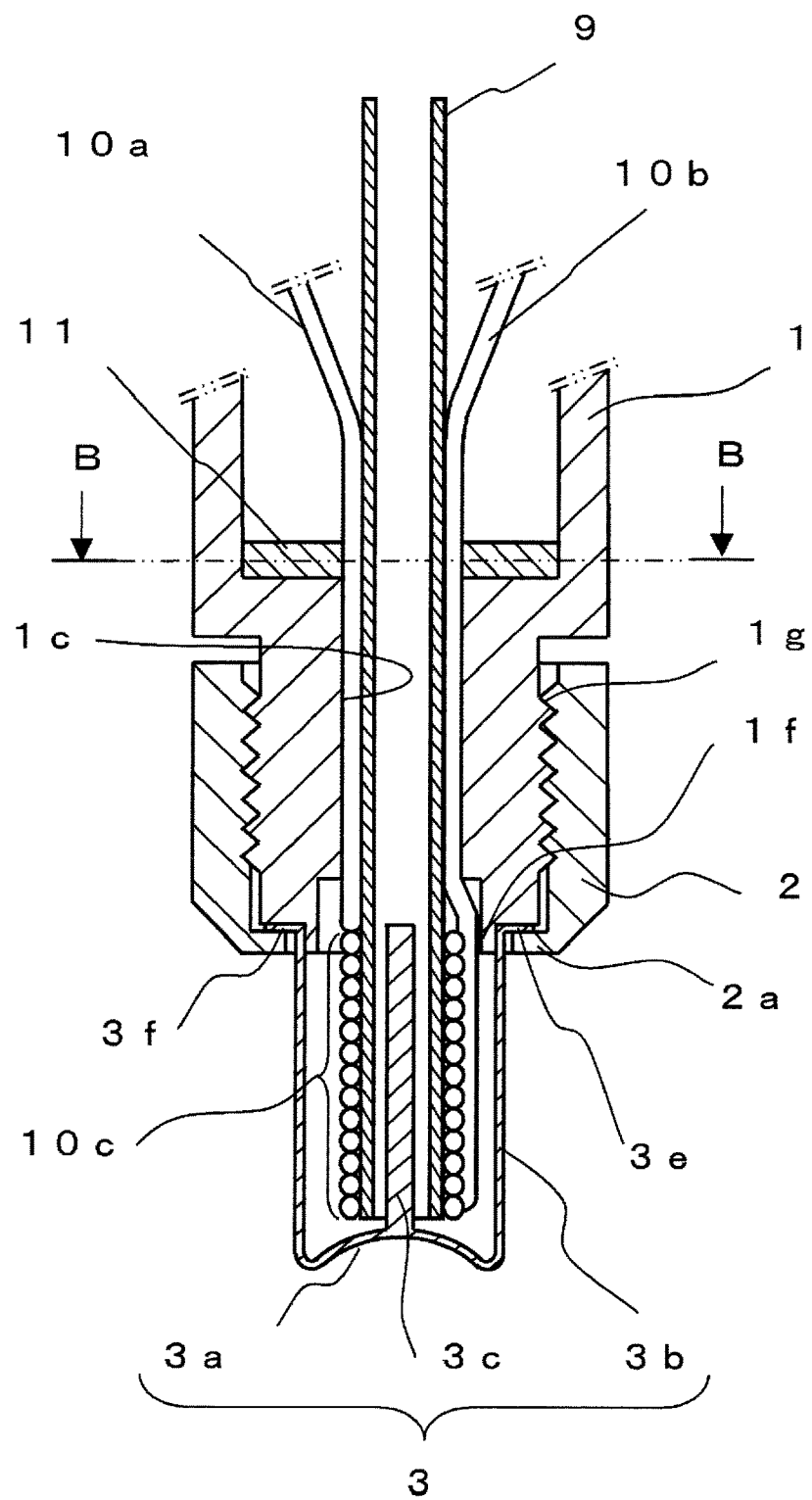
FIG. 2 is a cross-section view of the major part of a caulking unit of the plastic part thermal caulking device according to the first embodiment of the present invention.
Figure 3A:
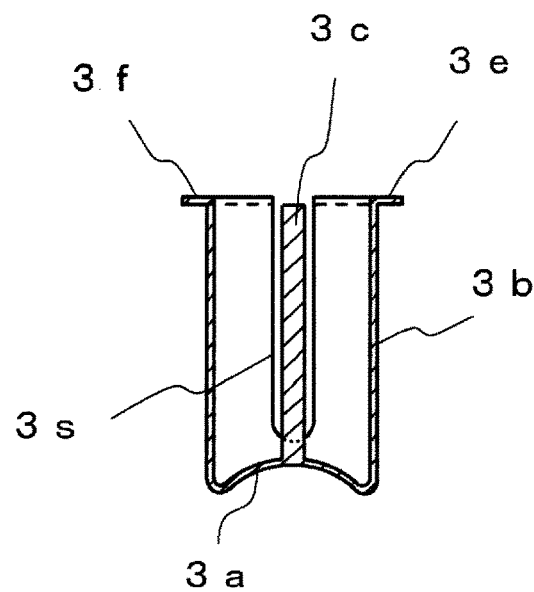
FIG. 3A is a cross-sectional view of a metal tip of the plastic part thermal caulking device according to the first embodiment of the present invention.
Figure 3B:
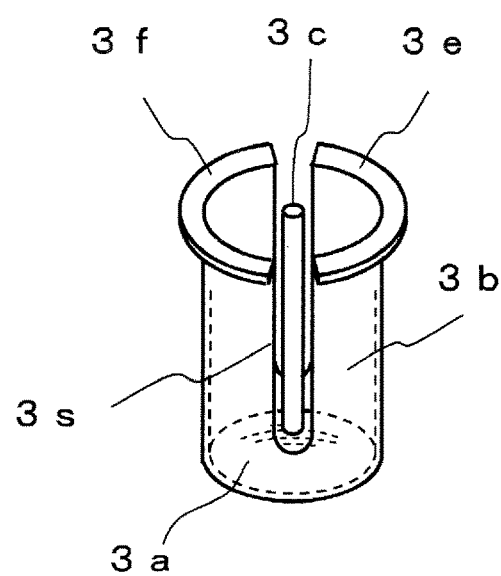
FIG. 3B is an external perspective view of the metal tip of the plastic part thermal caulking device according to the first embodiment of the present invention.

FIG. 2 is a cross-sectional view of the major part showing the metal tip 3 and the holder 1 and the holder cap 2 supporting the metal tip 3 (hereinafter referred to as a "caulking unit of a thermal caulking device") of the plastic part thermal caulking device according to the first embodiment of the present invention. The metal tip 3 is shown in the lowermost part or FIG. 2. FIG. 3A is a cross-sectional view of the metal tip 3, and FIG. 3B is an external perspective view of the metal tip 3.

For the understanding of the present invention, the metal tip 3 will be described first. The metal tip 3 as a whole has the shape of a closed-end cylinder, and the bottom pert functions as a plate-like pressing part 3a which presses the boss 7a of the plastic part. The plate-like pressing part 3a has an upwardly (toward the holder 1) convex spherical surface. A heating rod 3c is provided upright at the center of the pressing part 3a by welding or brazing, for example. A plate-like wall part 3b rises upward from the outer periphery of the pressing part 3a, and the wall part 3b is divided by a pair of slits 3s into two regions in the circumferential direction. Plate-like flanges 3e, 3f are formed at the upper end of the wall part 3b. The heating rod 3c is desirably made of a ferromagnetic material such as an iron-based alloy or a nickel-based alloy. This is because, as will be described in detail later, the Curie temperature is easy to regulate when the heating rod 3c is made of a ferromagnetic material.

Figure 4:
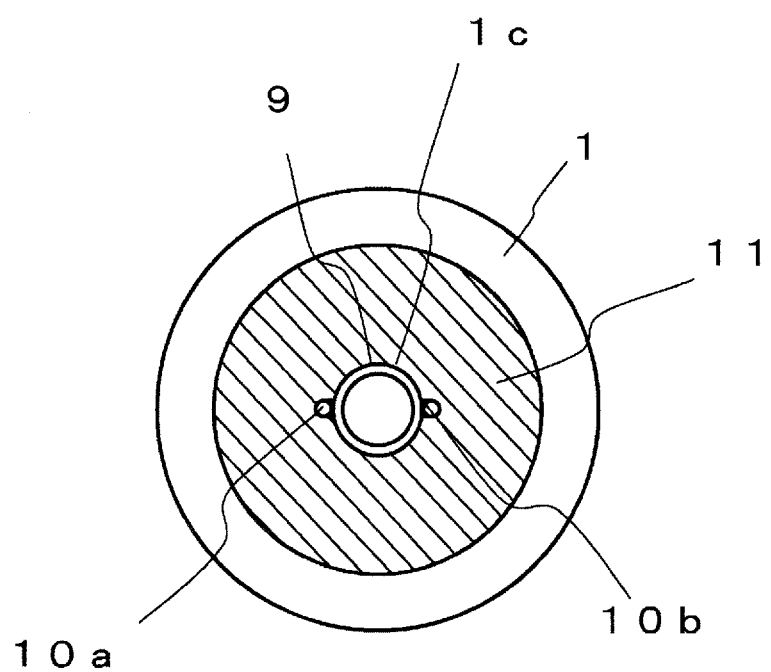
FIG. 4 is a cross-section view, along the line B-B of FIG. 2, of the caulking unit of the plastic part thermal caulking device according to the first embodiment of the present invention.

FIG. 4 is a cross-sectional view along the line B-B of FIG. 2, and shows the positional relation among the cooling pipe 9, the lead wires 10a, 10b, and a sealant 11 inside the metal tip 3. As shown in FIG. 4, the sealant 11 is provided on the bottom surface inside the holder 1. The clearance between the outer periphery of the cooling pipe 9 and the lead wires 10a, 10b is filled with the sealant 11, which is silicone rubber or high-density sponge, so that a cooling fluid delivered from the cooling pipe 9 does not spurts out through the clearance between the outer periphery of the cooling pipe 9 and the lead wires 10a, 10b.

Referring to FIG. 2, a thread 1g is cut on the outer periphery of a lower end part of the holder 1, and a step 1f which fits with the inner wall of the metal tip 3 is formed on the lower end surface of the holder 1. An odd-shaped hole 1c is formed from a center position in the lower end surface of the holder 1 to the bottom surface on the inside of the holder 1, and the cooling pipe 9 and the lead wires 10a, 10b are passed through the odd-shaped hole 1c. When seen in the cross-section along the line B-B as shown in FIG. 4, the odd-shaped hole 1c has a shape in which small-diameter holes for the lead wires 10a, 10b to pass through are formed on both sides of a large-diameter hole for the cooling pipe 9 to pass through.

The lead wires 10a, 10b are originally one lead wire, and obtained by continuously winding the lead wire on the outer periphery of a lower part in the longitudinal direction of the cooling pipe 9 in advance, and then pulling up both ends of the lead wire through the odd-shaped hole 1c along the cooling pipe 9 to the inside of the holder 1. The portion of the lead wire continuously wound on the outer periphery of the lower part of the cooling pipe 9 serves as a high-frequency induction coil 10c, and when a high-frequency current is applied to the lead wires 10a, 10b, an induced current flows through the high frequency induction coil 10c. Then, the heating rod 3c located inside the high-frequency induction coil 10c is heated by induction heating and generates high-temperature heat.

The inner surface of the wall part 3b of the metal tip fits on the outer peripheral surface of the step 1f of the holder 1, and the flanges 3e, 3f butt against the outer peripheral edge of the step 1f. With the metal tip 3 fitted with the step 1f of the holder 1, the holder cap 2 which is also made of plastic and has a female thread cut on the inside is screw-fastened. Since a metal tip holding portion 2a protruding inward is formed at the lower end of the holder cap 2, as the holder cap 2 is fastened to the holder 1, the metal tip 3 is held with the flanges 3e, 3f of the metal tip 3 clamped between the outer peripheral edge of the step 1f of the holder 1 and the metal tip holding portion 2a of the holder cap. When the metal tip 3 is thus attached to the holder 1, since the heating rod 3c is provided upright at the center of the pressing part 3a of the metal tip 3, the heating rod 3c is located inside the high-frequency induction coil 10c wound on the outer periphery of the cooling pipe 9.

Described below is one example of a thermal caulking method in the case where the boss 7a penetrating the metal plate 8 placed on the plastic part 7 is the object to be caulked by the thermal caulking device having the above configuration.

First, a high-frequency current is applied from the heating power source 5 to the lead wires 10a, 10b under the control of the controller 6 of the control unit. Then, an induced current flows from the lead wires 10a, 10b to the high-frequency induction coil 10c, and the heating rod 3c of the metal tip is heated by induction heating and generates high-temperature heat. The heat generated in the heating rod 3c transfers to the pressing part 3a of the metal tip. The heat having transferred to the pressing part 3a transfers to the wall part 3b and is partially released from the outer surface of the wall part 3b. However, since the pressing part 3a is supplied with heat from the heating rod 3c, the center of the pressing part 3a of the metal tip where the heating rod 3c is located is kept constantly at a high temperature. As for the heating time or the pressing part 3a, since induction heating is used, the temperature of the pressing part 3a rises instantly to a certain temperature as required for thermally caulking a plastic part.

At a point when an amount of heat as required for thermal caulking has been generated in the metal tip 3, or prior thereto, the holder 1 is lowered to press down the boss 7a by the pressing part 3a. As the heat of the pressing part 3a transfers to the boss 7a, the boss 7a is melted and softened, so that the head of the boss 7a assumes a shape expanded outward following the shape of the pressing part 3a, and as a result, the metal plate 8 is clamped between the head of the boss 7a and the plastic part 7. Thereafter, the controller 6 stops the application of a high-frequency current to the lead wire 10a, and supplies air at a temperature equal to or lower than normal temperature as cooling air (cooling fluid) from the cooling fluid supply machine 4 through the hose 4a into the holder 1. The cooling air supplied into the holder 1 is sprayed from the cooling pipe 9 toward the heating rod 3c and the pressing part 3a. The cooling air takes away heat from the heating rod 3c, the pressing part 3a, and the high-frequency induction coil 10c, and discharges the heat through the slits 3s of the metal tip 3, which are heat discharge holes, to the outside of the metal tip 3. Thus, the pressing part 3a and the heating rod 3c of the metal tip are instantly cooled. As a result, the boss 7a which has been temporarily melted and softened is cooled and solidified, which completes thermal caulking.

In the first embodiment of the present invention, the center part which repeatedly generates heat and cools, i.e., the heating rod 3c, is located inside the metal tip 3 protruding from the holder 1. The heating rod 3c is surrounded by the cooling pipe 9 which is also protruding from the holder 1, and the high-frequency induction coil 10c is disposed on the outer peripheral surface of the cooling pipe 9. As a high-frequency current is applied to the high-frequency induction coil 10c during heating, the heating rod 3c generates heat, and the pressing part 3a and the wall part 3b of the metal tip are heated from the heating rod 3c. After thermal caulking, as cooling air is delivered from the cooling pipe 9 toward the heating rod 3c and the pressing part 3a, the heating rod 3c is cooled, and the pressing part 3a and the wall part 3b of the metal tip are cooled.

Thus, since the heating rod of the metal tip provided upright at the center of the pressing part is heated and cooled first, the responsiveness to heating and cooling can be enhanced.

Since the thermal caulking device of this embodiment has the high-frequency induction coil 10c disposed inside the metal tip 3, the high-frequency induction coil 10c does not interfere with a worker performing caulking work or with the operation of a robot etc., so that the work efficiency can be enhanced.

Since the heating rod 3c, the pressing part 3a and the wall part 3b of the metal tip, and the high-frequency induction coil 10c which are repeatedly heated and cooled are located outside the holder 1 and the holder cap 2, the temperature of the holder 1 does not rise. Moreover, owing to the cooling effect of the cooling air passing through the inside of the holder 1 and the cooling pipe 9, the holder 1 and the holder cap 2 can be kept at such a temperature that a worker can grasp them.

In this embodiment, the structure in which the screw of the holder cap 2 is fastened to thereby attach the metal tip 3 to the holder 1 is shown in FIG. 2. That is, the metal tip 3 fixed on the holder 1 can be easily replaced with another metal tip by loosening the screw of the holder cap 2 and removing the holder cap 2 from the holder 1.

As a method for attaching/removing the holder 1 and the holder cap 2 to/from each other, methods which allow them to be attached or removed by a single action can also be used other then screw connection using a male thread and a female thread provided in the holder 1 and the holder cap 2. A structure can be used which can attach or remove the holder 1 and the holder cap 2 by integrating or disassembling them, for example, a structure in which the holder 1 has a protruding pin on the outer periphery and the holder cap 2 is provided with a cam groove to engage with the pin, and the pin and the cam groove are engaged with each other.

Figure 5:
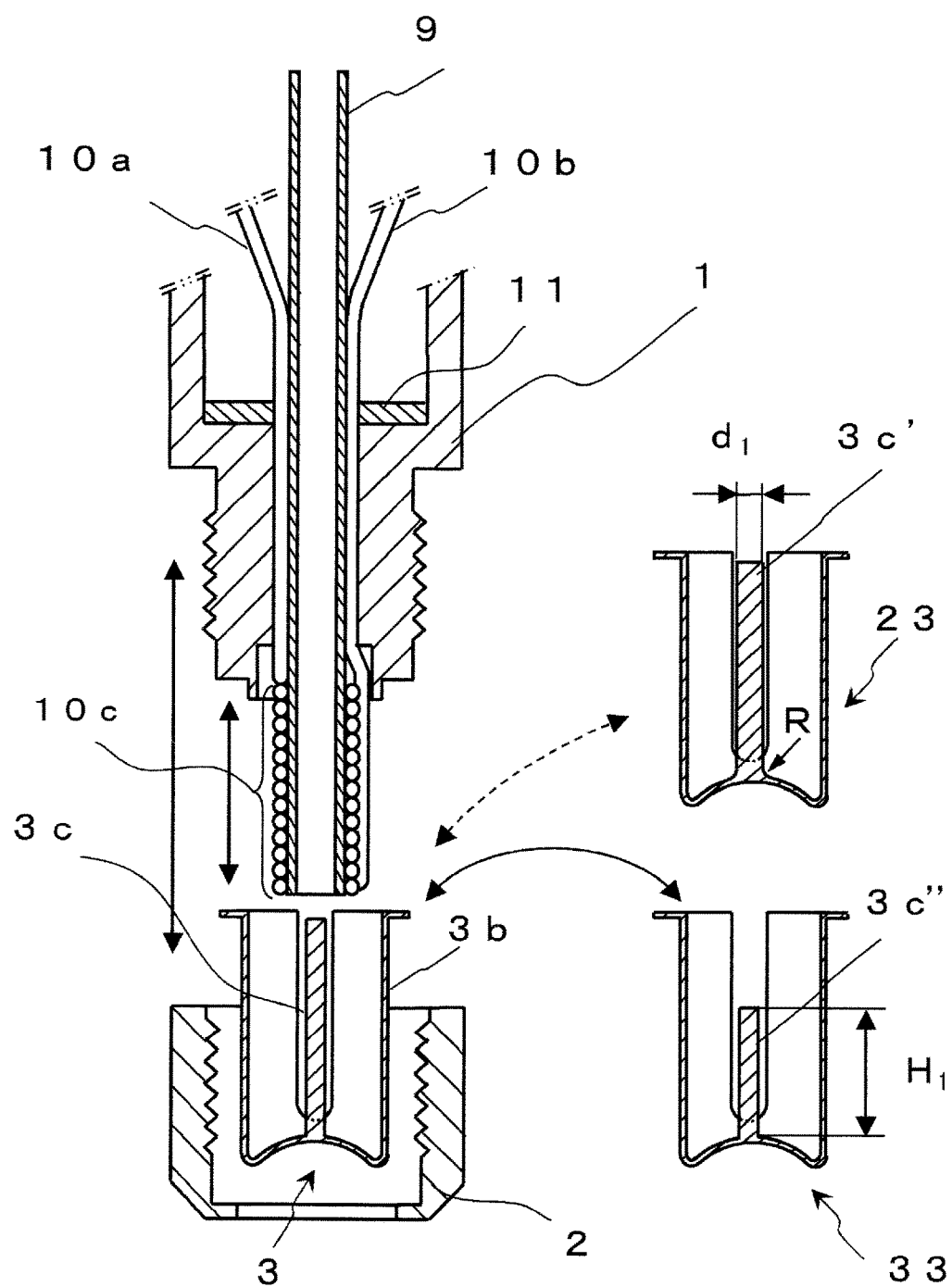
FIG. 5 is a view showing an exploded cross-sectional view of the caulking unit of the plastic part thermal caulking device according to the first embodiment of the present invention, along with a cross-sectional view of replacement metal tips.

With regard to the replacement of the metal tip, FIG. 5 shows an exploded cross-sectional view of the caulking unit of the plastic part thermal caulking device according to the first embodiment of the present invention in which the screw of the holder cap 2 is loosened and the holder cap 2 is removed from the holder 1, along with a cross-sectional view of other replacement metal tips.

As described already, the caulking unit of the thermal caulking device of this embodiment has a structure in which the flanges 3e, 3f of the metal tip 3 are clamped and held between the holder 1 and the holder cap 2 which are screw-connected to each other. Accordingly, as shown in FIG. 5, loosening the screw of the holder cap 2 and removing the holder cap 2 from the holder 1 can remove the metal tip 3. As indicated by the dashed or solid double-headed arrow in FIG. 5, the metal tip 3 can be replaced with another metal tip. For example, thermal caulking can be performed using such as a metal tip 23 of which the diameter of the heating rod 3c is large and the root of the heating rod 3c and the pressing part 3a are connected to each other through a curved surface (rounded corner), or a metal tip 33 of which the length of the heating rod 3c is short.

Figure 6A:
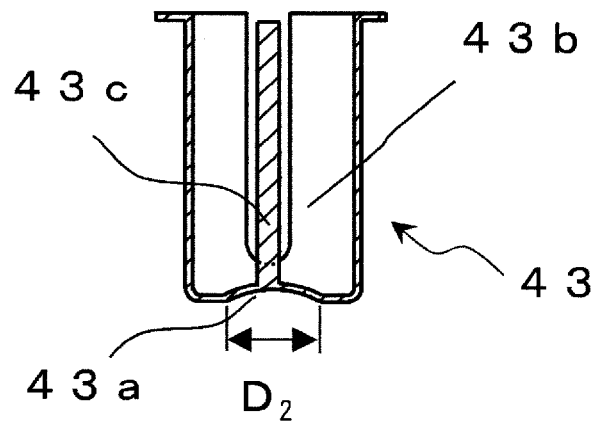
FIG. 6A is a cross-sectional view or another replacement metal tip of the plastic part thermal caulking device according to the first embodiment of the present invention.
Figure 6B:
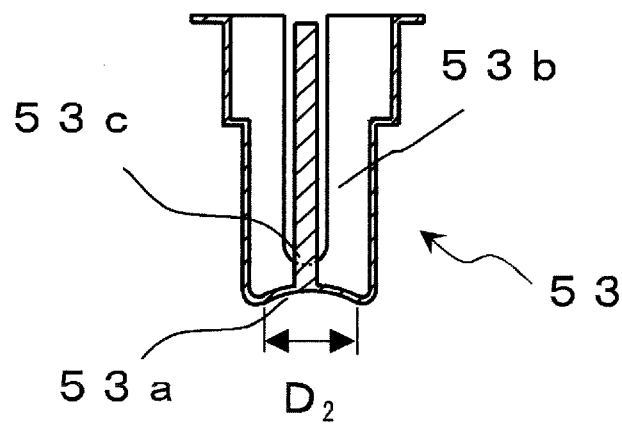
FIG. 6B is a cross-sectional view of another replacement metal tip of the plastic pert thermal caulking device according to the first embodiment of the present invention.
Figure 6C:
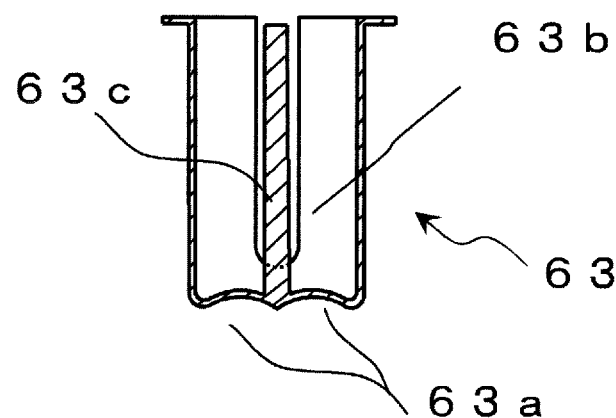
FIG. 6C is a cross-sectional view of another replacement metal tip of the plastic part thermal caulking device according to the first embodiment of the present invention.

FIG. 6A to FIG. 6C each show a cross-sectional view of yet another replacement metal tip of the plastic part thermal caulking device according to the first embodiment of the present invention. A metal tip 43 of FIG. 6A has an upwardly curved surface in an area having a diameter $D_2$ in a center part of a pressing part 43a. The peripheral edge portion other than this area is a flat surface, and the portion continuous with a wall part 43b is connected as a curved surface. This metal tip 43 is convenient when making the head of the boss 7a of the plastic part smaller.

A metal tip 53 of FIG. 6B is a two-step metal tip with a wall part 53b varied in diameter. Since the leading end of the wall part 53b is small, this metal tip 53 has an effect that the visibility near the leading end of the metal tip 53 is good and positioning during thermal caulking work is easy.

A metal tip 63 of FIG. 6C has a pressing part 63a which is downwardly convex at the center of the caulking-side surface and upwardly convex around the center of the caulking-side surface. This metal tip 63 has an effect that thermal caulking can be performed so as to press down the center of the boss 7a by the center of the pressing part 53a.

Figure 7:
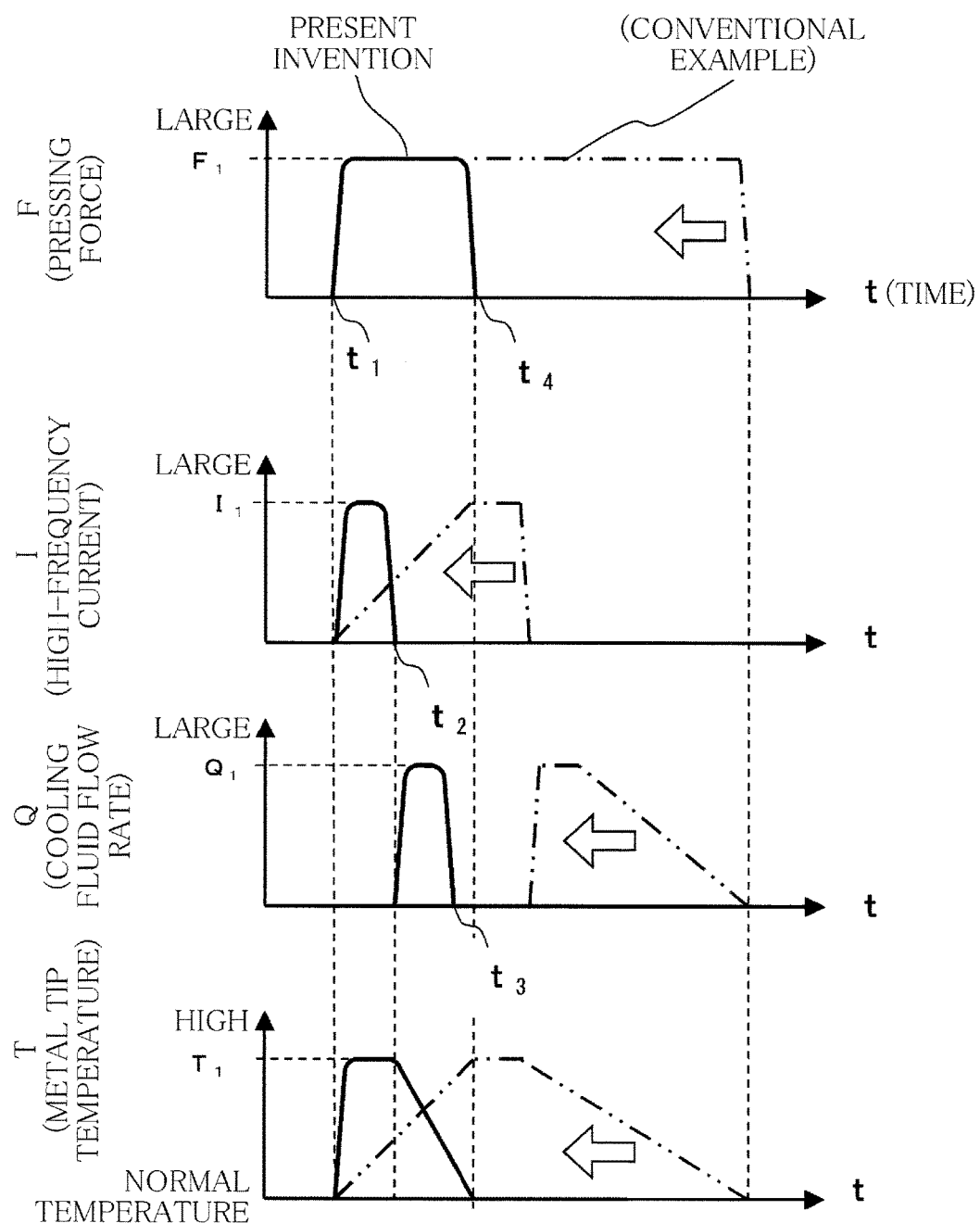
FIG. 7 is a view showing changes over time in pressing force, high-frequency current, cooling fluid flow rate, and metal tip temperature during caulking work by the plastic part thermal caulking device according to the first embodiment of the present invention.

FIG. 7 shows changes over time in pressing force, high-frequency current, cooling fluid flow rate, and metal tip temperature during caulking work by the plastic part thermal caulking device according to the first embodiment of the present invention. With the abscissa serving as a time axis, FIG. 7 shows changes according to time in pressing force, high-frequency current, cooling fluid flow rate, and metal tip temperature. In FIG. 7, the pressing force (F) between the pressing part 3a of the metal tip and the boss 7a of the plastic part 7 starts to increase to a predetermined pressure ($F_1$) at time ($t_1$). At the same time, the high-frequency current (I) starts to be applied until a predetermined current ($I_1$) is reached, so that the metal tip 3 starts to generate heat and the temperature (T) of the metal tip starts to rise. Thereafter, at time ($t_2$) when the temperature of the metal tip has reached a predetermined temperature ($T_1$), the high-frequency current (I) is stopped, and instead a cooling fluid (Q) is passed in a predetermined amount ($Q_1$) for a predetermined time, until time ($t_3$). Then, the metal tip is cooled and decreases in temperature. When the temperature of the metal tip has returned to normal temperature, thermal caulking is considered as completed, and the metal tip 3 is raised and separated from the boss 7a (time ($t_4$)).

For the temperature regulation of the present invention, Curie temperature automatic regulation is performed under the control of the controller 6. Curie temperature automatic control is described as follows. When a current is applied to a high-frequency coil by a high-frequency power source, magnetism is generated around the high-frequency coil. This magnetism causes an eddy current due to the skin effect to flow through the magnetic layer of a heating rod provided in a metal tip, so that the magnetic layer generates heat under Joule heating. This heat transfers through the heating rod, which has high thermal conductivity, to the pressing part. In particular, when the magnetic layer of the heating rod is made of a material having a Curie point, the magnetic properties diminish when the heating rod is heated to or above the Curie point, so that the eddy current due to the skin effect decreases and the Joule heat decreases. When the temperature falls below the Curie point, the magnetic properties are restored and the Joule heat increases again. Curie temperature automatic regulation is about maintaining a predetermined temperature through repetition of this process. In FIG. 7, the metal tip temperature (T) is kept at the predetermined temperature ($T_1$) because Curie temperature automatic regulation is used.

Figure 25:
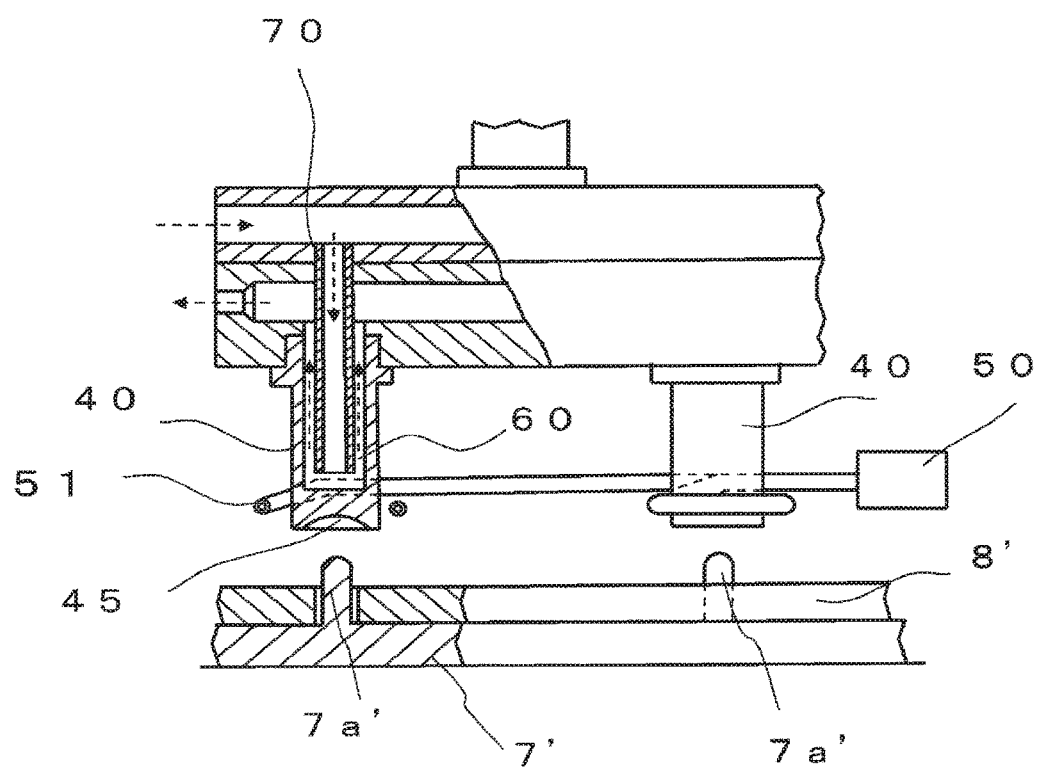
FIG. 25 is a schematic configurational view of a second conventional plastic part thermal caulking device.
Figure 26:
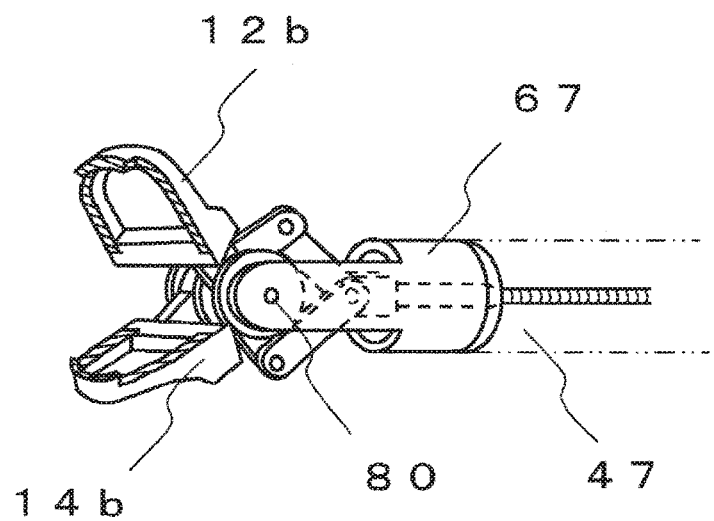
FIG. 26 is a perspective view of a catheter tube with an opening-closing forceps part which is a conventional plastic part to be thermally caulked.
Figure 27:
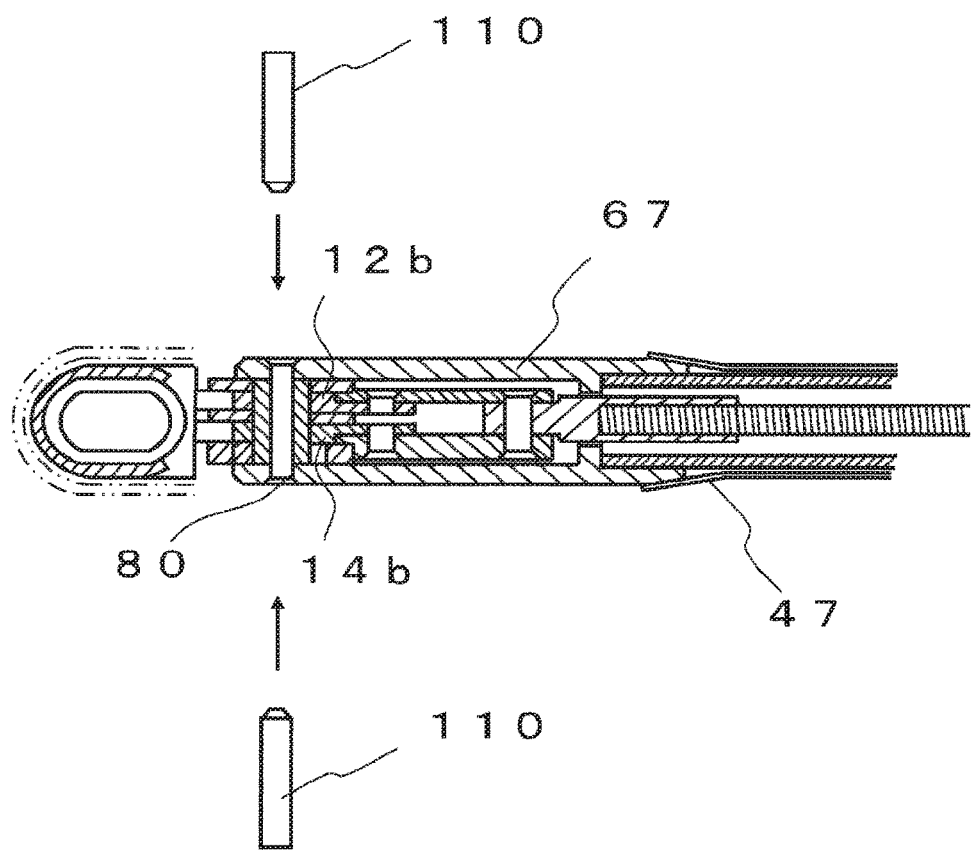
FIG. 27 is a view showing a state in which a support shaft of the catheter tube with an opening-closing forceps part which is a conventional plastic part to be thermally caulked is thermally caulked.

For comparison, the two-dot chain lines in FIG. 7 indicate the values of the pressure force etc. in the case where, for example, the conventional thermal caulking device of FIG. 25 is used. Although the same high-frequency induction heating and cooling with a cooling pipe are used, the conventional device takes time to raise the temperature of the metal tip 40 and to cool the metal tip 40 due to the large heat capacity of the metal tip 40, and as indicated by the two-dot chain line in FIG. 7, it takes a long time to raise the temperature of the metal tip 40 to a predetermined temperature and to return the temperature back to normal temperature. It is obvious from FIG. 7 that, according to the present invention, the metal tip 3 has a small heat capacity and therefore the temperature of the metal tip 3 rises to a predetermined temperature in a short time and returns to normal temperature in a shorter time than the conventional metal tip.

In this embodiment, the heating rod 3c is provided at the center of the pressing part 3a of the metal tip 3, and the heating rod 3c is instantly heated and cooled. Therefore, the heat capacity of the heating rod 3c can be set to be just large enough for thermal caulking. Accordingly, the metal tip 3 can be made thinner and smaller, so that a reduction in size and weight of the device can be achieved. Moreover, as the heat capacity of the heating rod 3c is reduced to a minimum heat capacity required for thermal caulking, electrical power required for heating can also be reduced, so that a low-output, energy-saving device can be realized.

When the boss 7a is melted and then cooled and solidified, the boss 7a is cooled and solidified sequentially from the periphery of the boss 7a, which has been melted and crushed to spread around, toward the center. When the center of the boss 7a is cooled and solidified last, the boss 7a shrinks while the center part thereof is solidifying, resulting in a larger caulking force. If the heating rod 3c located at the center of the pressing part 3a has a larger heat capacity than the other parts, the center part of the boss 7a can be cooled last reliably. Thus, an effect that the caulking force increases as the boss 7a shrinks while the center part thereof is solidifying can be obtained.

If produced in advance in a larger length, the heating rod 3c is easy to process to reduce the length and thereby reduce the heat capacity. If a larger heat capacity is required, the metal tip can be replaced with a metal tip having a thicker heating rod.

In this embodiment, the slits 3s of the metal tip function solely as open holes through which the cooling air delivered inside the metal tip is discharged. That is, the slits 3s are heat discharge holes through which heat taken away by the cooling air from the heating rod 3c, the pressing part 3a, and the high-frequency induction coil 10c is discharged. In this embodiment, since the pressing part 3a is heated from the center through the heating rod, the problem with the conventional device that the temperature of the metal tip becomes uneven due to the slits 3s provided therein is prevented.

A modified example of the first embodiment will be described below. FIG. 8 shows the modified example of the first embodiment. The thermal caulking device of the first embodiment of the present invention already shown in FIG. 1 is used by a worker grasping the holder 1 of the caulking unit and pressing the pressing part 3a of the metal tip against the leading end of the boss 7a. In this case, since the work is performed by a human, the pressing force may vary among workers. In the modified example of the first embodiment, therefore, the holder 1 is pressed through a compression spring 150 so that the pressing force does not vary.

Figure 8A:
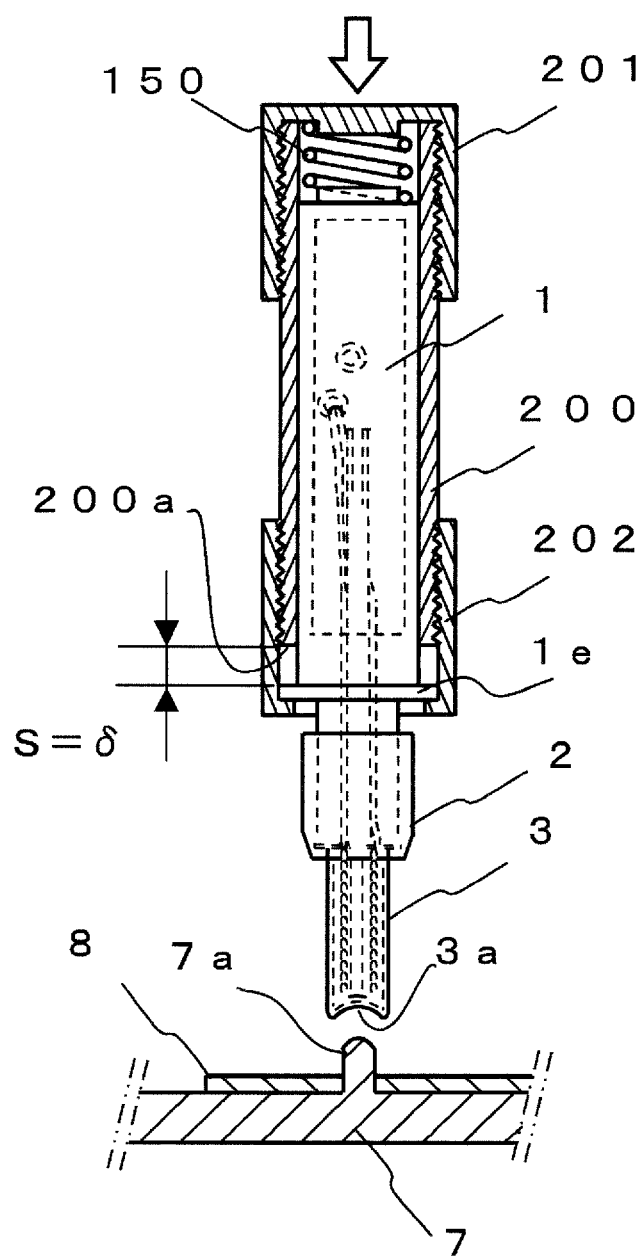
FIG. 8A is a view showing a state before caulking work in a modified example of a holder of the plastic part thermal caulking device according to the first embodiment of the present invention.

That is, in the modified example of the first embodiment of the present invention, as shown in FIG. 8A, a slide holder 200 which is cylindrical and slidable in the longitudinal direction of the holder 1 is provided on the outer periphery of the holder 1. The compression spring 150 is provided on the upper end surface of the holder 1. A slide holder cap 201 which regulates the position of the compression spring 150 is integrally attached to an upper part of the slide holder 200. A flange 1e is provided at the lower end of the holder 1, and a slide holder stopper 202, of which the position is regulated by the flange 1e, is integrally attached to a lower part of the slide holder 200.

FIG. 8A shows a state before caulking work. In a state where a worker is merely grasping the slide holder 200, as shown in FIG. 8A, the compression spring 150 is pushing up the slide holder cap 201 to the upper side of the holder 1, and the lower end of the slide holder stopper 202 is in contact with the flange 1e of the holder. Thus, in this state, there is a clearance (S) formed between the flange 1e of the holder and the lower end of the slide holder 200.

It is preferable that screw connection is used to attach the slide holder 200 and the slide holder cap 201 to each other and attach the slide holder 200 and the slide holder stopper 202 to each other. This is because the amount of compression of the compression spring 150 and the clearance (S) between the flange 1e of the holder and the lower end of the slide holder 200 can be adjusted by adjusting the amount of screwing of screw connection. Otherwise, these parts may be bonded together with an adhesive or welded together if it is not necessary to adjust the amount of compression of the compression spring 150 or the clearance (S) between the flange 1e of the holder and the lower end of the slide holder 200.

Figure 8B:
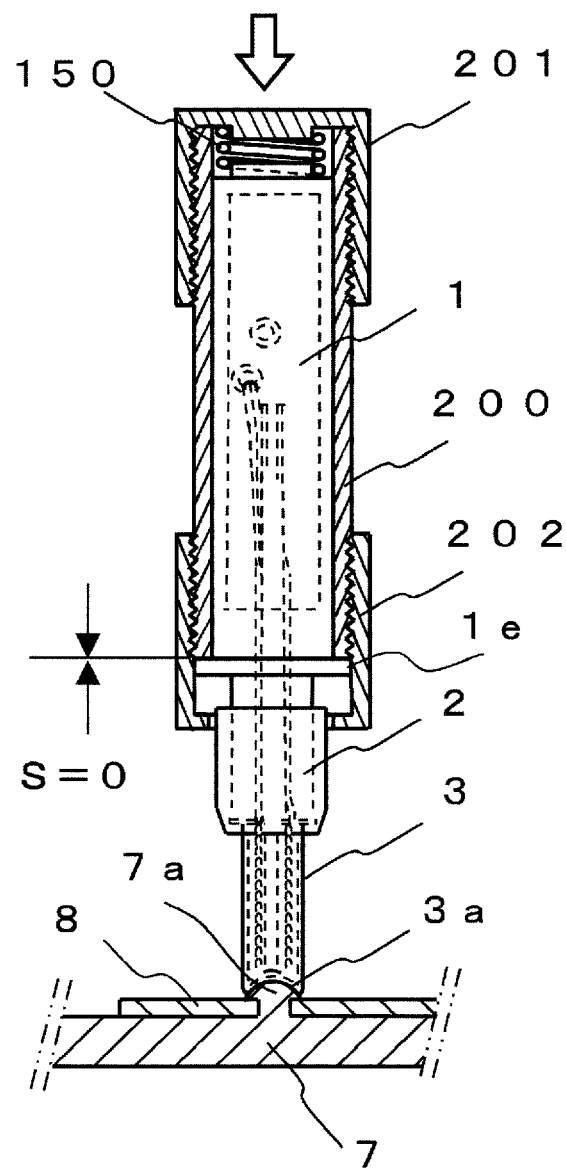
FIG. 8B is a view showing a state during caulking work in the modified example of the plastic part thermal caulking device according to the first embodiment of the present invention.

Next, as shown in FIG. 8B, when the worker grasps the slide holder 200 and presses it downward, the pressing part 3a of the metal tip hits the leading end of the boss 7a. Then, heat of the metal tip 3 transfers to the boss 7a and thermal caulking starts. When the pressing force is continuously applied to the slide holder 200, the slide holder cap 201 compresses the compression spring 150, so that the holder 1 is pressed down by the urging force of the compression spring 150. When the slide holder 200 is lowered, a leading end 200a of the slide holder hits the flange 1e of the holder 1. Unless the worker presses with a larger force at the point when the leading end 200a of the slide holder 200 hits the flange 1e at the lower end of the holder 1, the pressing force is kept at the pressing force which compresses the compression spring 150 in a predetermined amount. Then, thermal caulking work can be performed with an almost constant pressing force. Thus, in the modified example of the first embodiment of the present invention, variation in pressing force during thermal caulking work by a worker is eliminated.

In the modified example of the first embodiment of the present invention, the slide holder 200, the slide holder cap 201, the slide holder stopper 202, and the compression spring 150 correspond to the pressing operation means when a worker grasps and uses the thermal caulking device of the present invention.

Although description about the use of modified examples of the metal tip as shown in the first embodiment will be omitted in the following description of a second embodiment to a seventh embodiment, the modified examples can be similarly applied to any of these embodiments.

Second Embodiment

Figure 9:
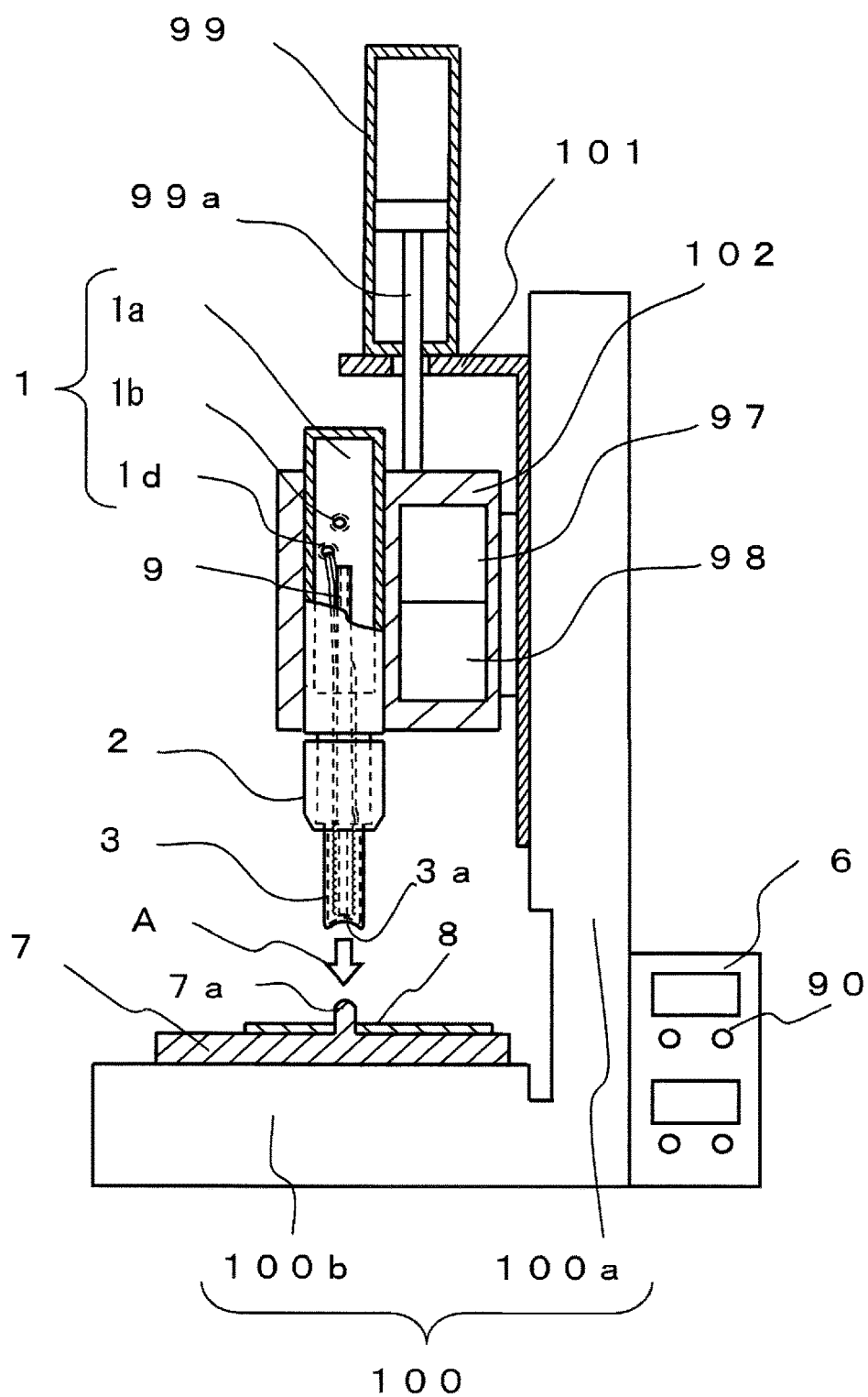
FIG. 9 is an overall configurational view showing a plastic part thermal caulking device according to a second embodiment of the present invention.

FIG. 9 is an overall configurational view showing a plastic part thermal caulking device according to a second embodiment of the present invention. In the plastic part thermal caulking device according to the second embodiment of the present invention, the holder 1 with the metal tip 3 attached thereto is supported by a pressing operation mechanism, such as an air cylinder, so as to be movable in the vertical direction. The second embodiment is characterized in that the pressing part 3a of the metal tip 3 is pressed down to the leading end of the boss 7a through the operation of the pressing operation mechanism such as an air cylinder. Since the pressing work is not manual work performed by a worker but machine work performed by the thermal caulking device, a predetermined pressing force managed to be constant can be applied.

In FIG. 9, a housing 100 of the thermal caulking device has an L-shape in which a column 100a extending in the vertical direction in the sheet plane of FIG. 9 and an anvil 100b extending in the left-right direction in the sheet plane of FIG. 9 are integrally coupled to each other. An air cylinder bracket 101 is attached to the column 100a. An air cylinder 99 is attached to the air cylinder bracket 101, with a rod 99a facing downward. A slide unit 102 is attached at the leading end of the rod 99a, and the slide unit 102 can move up and down along the column 100a.

A heating power source 97 which supplies electrical power to the holder 1 and the high-frequency induction coil, and a cooling fluid supply part 98 are attached to the slide unit 102. Although not shown, lead wires inside the holder 1 are connected to the heating power source 97, and the cooling pipe 9 is connected to the cooling fluid supply part 98. The metal tip 3 is clamped by the holder 1 and the holder cap 2 and is held with the pressing part 3a facing downward. In FIG. 9, the controller 6 is disposed on the right side of the housing 100. Although this is not shown either, the controller 6 is connected to the heating power source 97 and the cooling fluid supply part 98 inside the column 100a. On the anvil 100b, the plastic part 7 to be thermally caulked and the metal plate 8 are placed on top of one another. The boss 7a of the plastic part 7 is protruding from the hole of the metal plate 8. Alternatively, the heating power source 97 and the cooling fluid supply part 98 may be disposed next to the controller 6, integrally with the controller 6, instead of in the slide unit 102.

When a worker selects thermal caulking conditions by operating an input/output part 90 of the controller 6 and starts thermal caulking work, under the control of the controller 6, the metal tip 3, which is heated by a current applied from the heating power source 97 is pressed down along with the slide unit 102 by the air cylinder 99, which is the pressing operation mechanism, as indicated by the arrow A in FIG. 9. Then, the pressing part 3a of the metal tip 3 hits the leading end of the boss 7a and thermally caulks the boss 7a. The application of a current by the heating power source 97 is stopped after a predetermined time, and a cooling fluid is delivered from the cooling fluid supply part 98 to the cooling pipe 9 to cool the heating rod 3c, the pressing part 3a, and the wall part 3b of the metal tip 3. Thereafter, the metal tip 3 along with the holder 1 is moved upward by the air cylinder 99 to finish the thermal caulking work. The worker can replace the plastic part 7 and the metal plate 8 on the anvil 100b with new ones, and perform thermal caulking work by the same procedure.

Figure 10:
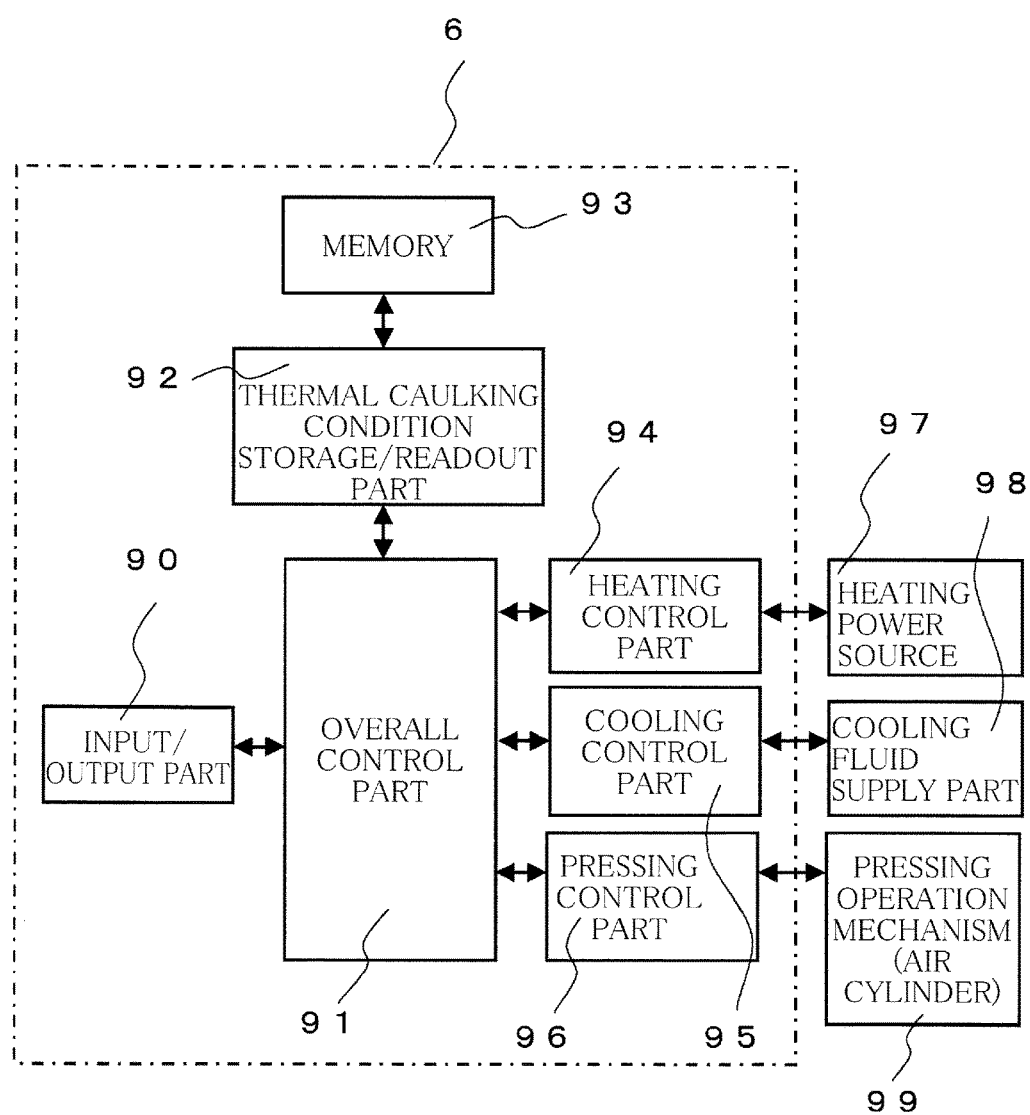
FIG. 10 is a control block diagram of the plastic part thermal caulking device according to the second embodiment of the present invention.

FIG. 10 shows a control block diagram of the plastic part thermal caulking device according to the second embodiment of the present invention. The box of the one-dot chain line in FIG. 10 indicates a range corresponding to the controller 6 of FIG. 9. Inside the controller 6 are an overall control part 91, a thermal caulking condition storage/readout part 92 connected to the overall control part 91, and a memory 93 linked to the thermal caulking condition storage/readout part 92. Moreover, a heating control part 94, a cooling control part 95, and a pressing control part 96 are each linked to the overall control part 91, and the thermal caulking device controls thermal caulking through cooperation of the control parts 94, 95, 96.

Specifically, the heating power source 97, the cooling fluid supply part 98, and the air cylinder 99 are controlled by the heating control part 94, the cooling control part 95, and the pressing control part 96, respectively. During thermal caulking, information on thermal caulking conditions selected by the worker in the input/output part 90 is received by the overall control part 91, and required information according to the thermal caulking conditions is stored in or read out from the memory 93 through the thermal caulking condition storage/readout part 92, and commands are sent to the heating control part 94, the cooling control part 95, and the pressing control part 96.

FIG. 11 shows one example of data configuration for thermal caulking conditions stored in the memory 93. For the outer diameter (X) of the boss to be caulked, the caulking amount (Y) of the boss, and the material (Z) of the boss, a plurality of sets of thermal caulking conditions, Condition 1, Condition 2, Condition 3, Condition 4, and Condition 5, are shown in descending order of the score. For each set of thermal caulking conditions, toe values of the following parameters: pressing part shape (K), wall part outer diameter (D), wall part thickness (N), heating rod diameter (d), heating rod height (H), pressing force (F), high-frequency current (I), cooling fluid flow rate (Q), metal tip temperature (T), pressing/current application start time ($t_1$), current application end/cooling start time ($t_2$), cooling end time ($t_3$), and pressing end time ($t_4$) (the values are represented by the symbols in FIG. 11) are stored along with the scores in the form of a table in the memory 93, and the overall control part 91 controls thermal caulking by reading out the specifications of the items according to the conditions selected by the worker.

For example, when the worker inputs the diameter (X) of the boss to be thermally caulked, the caulking amount (Y), and the material (Z) of the boss in the input/output part 90, under the command of the overall control part 91, the thermal caulking condition storage/readout part 92 reads out the conditions to be used from the memory 93 and presents the conditions to the worker in descending order of the score. When the worker selects the conditions through the input/output part 90 and starts thermal caulking, the overall control part 91 commands the heating control part 94, the cooling control part 95, and the pressing control part 96 according to the selected thermal caulking conditions to actuate the heating power source 97, the cooling fluid supply part 98, and the air cylinder 99 and thereby execute thermal caulking work.

In FIG. 9, the example has been shown in which the holder 1 with the metal tip 3 attached thereto is attached to the slide unit 102 and the slide unit 102 is supported by the pressing operation mechanism, such as the air cylinder 99, so as to be movable in the vertical direction. However, as shown in FIG. 8, the holder 1 with the slide holder 200, the slide holder cap 201, the slide holder stopper 202, and the compression spring 150 attached thereto may be attached to the slide unit 102. Then, thermal caulking can be performed using a spring force exerted by the compression of the compression spring.

In this embodiment, the metal tip having the metal rod serving as the heating rod welded or brazed at the center of the pressing part is used, and a high-frequency current is applied to the high-frequency induction coil set on the outer periphery of the heating rod to thereby perform thermal caulking through induction heating. Thus, the basic effects of this embodiment are the same as those of the first embodiment.

Third Embodiment

Figure 12:
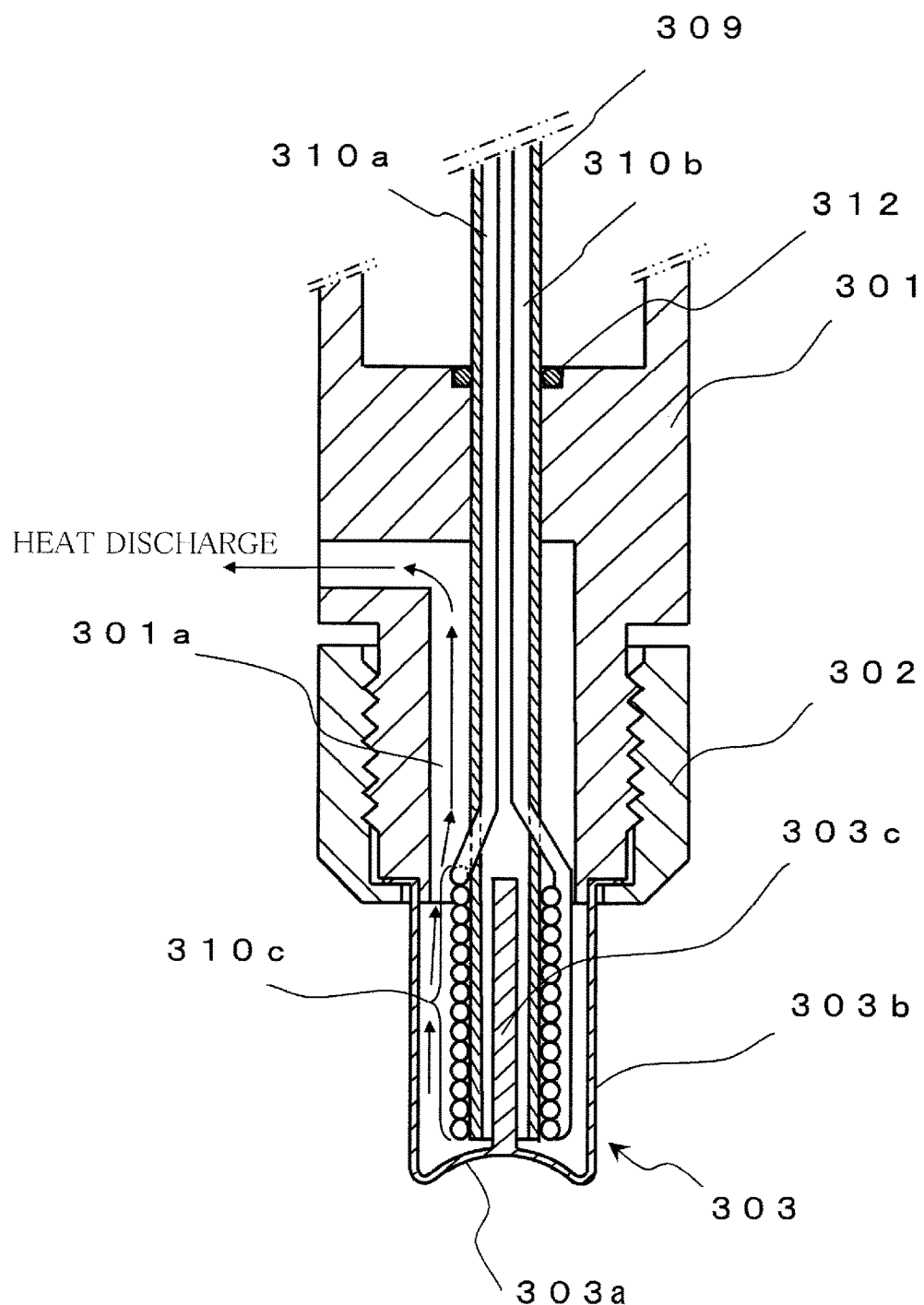
FIG. 12 is a cross-section view of the major part of a caulking unit of a plastic part thermal caulking device according to a third embodiment of the present invention.

FIG. 12 shows a cross-sectional view of the major part of a thermal caulking unit of a plastic part thermal caulking device according to a third embodiment of the present invention.

As shown in FIG. 12, the third embodiment of the present invention is characterized in that portions of lead wires 310a, 310b which are not a winding portion of a high-frequency induction coil 310c are placed inside a cooling pipe 309. Each time a cooling fluid is passed through the cooling pipe 309, the portions of the lead wires 310a, 310b which are not the winding portion of the high-frequency induction coil 310c are cooled inside the cooling pipe 309, which has an effect that heat generated in the high-frequency induction coil 310c does not transfer to where it is not intended.

Instead of a heat discharge slit (opening), such as a slit, provided in a metal tip 303, a heat discharge hole 301a is bored in a holder 301. The heat discharge hole 301a is a hole having an L-shaped cross-section formed by a longitudinal hole extending from the leading end of the holder 301 in the axial direction and a lateral hole extending from the longitudinal hole to the side surface of the holder 301.

More specifically, the high-frequency induction coil 310c is wound on the outer periphery of the cooling pipe 309 in a lower part of the cooling pipe 309, and a hole is formed at two positions in the side surface on the upper side from the high-frequency induction coil 310c. The pair of lead wires 310a, 310b extending from the high-frequency induction coil 310c are inserted into the cooling pipe 309 through the holes bored in the cooling pipe 309. Although not shown in detail, it is preferable that the clearance between the lead wires 310a, 310b and the holes of the cooling pipe 309 is closed with a heat-resistant adhesive etc.

While the holder 301 has almost the same outer shape as the holder 1 of the first embodiment, the longitudinal hole portion of the heat discharge hole 301a communicating with the cavity inside the metal tip 303 is bored in the axial direction of the cooling pipe 309. In addition, an O-ring 312 fills and seals the clearance between the cooling pipe 309 and the holder 301.

In the third embodiment of the present invention, cooling air which is a cooling fluid passed from the cooling pipe 309 into the cavity of the metal tip 303 flows along the outer surface of the heating rod 303c, and after colliding with the pressing part 303a, rises along a wall part 303b before flowing via the heat discharge hole 301a to the outside of the holder 301. Thus, heat of the heating rod 303c and the pressing part 303a of the metal tip as well as of the high-frequency induction coil 310c is discharged. In this embodiment, since heat transfers to the holder 301 and the holder cap 302 during heat discharge, a longer heat discharge time is provided to return the temperatures of the holder 301 and the holder cap 302 to normal temperature.

In the third embodiment, the same effects as those of the first embodiment can be achieved, and since the heat discharge slit is not provided in the wall part 303b of the metal tip 303, the mechanical strength of the metal tip 303 can be enhanced. Thus, there is an advantage in that the metal tip 303 does not deform even when the boss 7a is pressed hard with the metal tip 303 which is further reduced in plate thickness.

Fourth Embodiment

Figure 13:
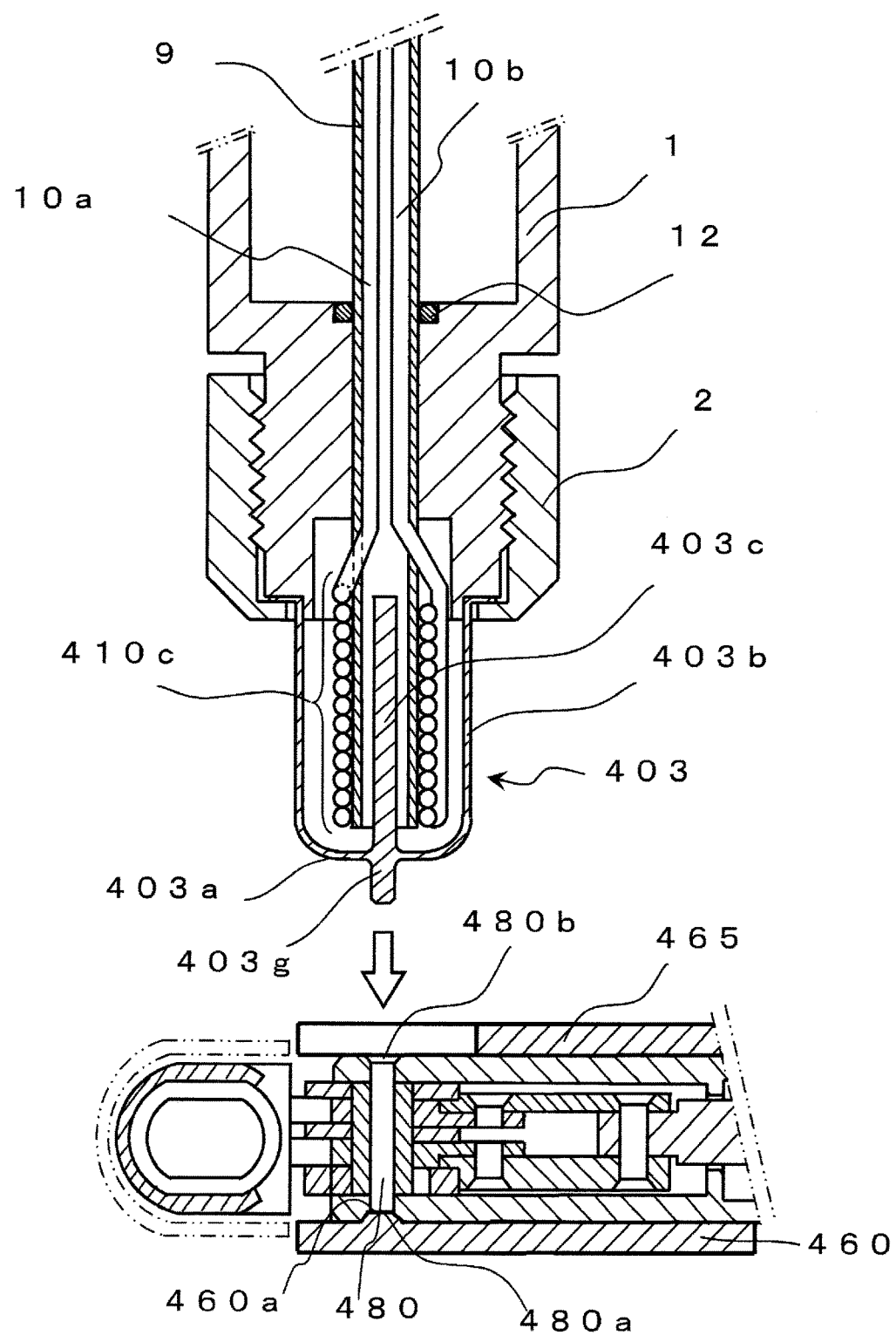
FIG. 13 is a cross-sectional view showing the major part of a caulking unit of a plastic part thermal caulking device according to a fourth embodiment of the present invention, in juxtaposition with an object to be caulked.

As shown in FIG. 13, a fourth embodiment of the present invention is characterized in that a heating rod 403c is provided at the center on the inside of a pressing part 403a of a metal tip 403, and that the heating rod 403c is protruded as a heating rod leading end 403g to the outside of the pressing part 403a.

FIG. 13 is a cross-sectional view showing the major part of a thermal caulking unit of the plastic part thermal caulking device according to the fourth embodiment of the present invention, in juxtaposition with an object to be caulked. On the lower side from the thermal caulking unit of FIG. 13, a leading end part of a catheter tube is shown which is placed on an anvil 460 and positioned and fixed by a pressing and fixing member 465 with a hole. One end 480a of a plastic support shaft 480 at the leading end part of the catheter tube is supported on a convex portion 460a of the anvil 460, while the other end 480b of the support shaft faces the heating rod leading end 403g protruding from the pressing part 403a of the metal tip.

The heating rod leading end 403g is a portion of the heating rod 403c protruded further in the pressing direction than the pressing part 403a, and the heating rod leading end 403g has a pressing surface. When the heating rod 403c is induction-heated by a high-frequency induction coil 410c, the thermal energy generated in the heating rod 403c transfers to the heating rod leading end 403g protruding from the pressing part 403a of the metal tip. When the heating rod leading end 403g thermally caulks the other end 480b of the support shaft at the leading end part of the catheter tube under the best thermal caulking conditions read out from the plurality of sets of thermal caulking conditions stored in advance in the thermal caulking condition storage means, the other end 480b of the small support shaft is thermally caulked into the best state.

Thus, according to the configuration in which the heating rod leading end 403g serves as the pressing surface, the same effects as those of the first embodiment can be obtained, as well as the pressing surface can be reduced. This has an effect that it is possible to stably and precisely thermally caulk small plastic parts, like a plastic support shaft at the leading end of a catheter tube to be inserted into the body, under the best thermal caulking conditions stored in advance.

Figure 14:
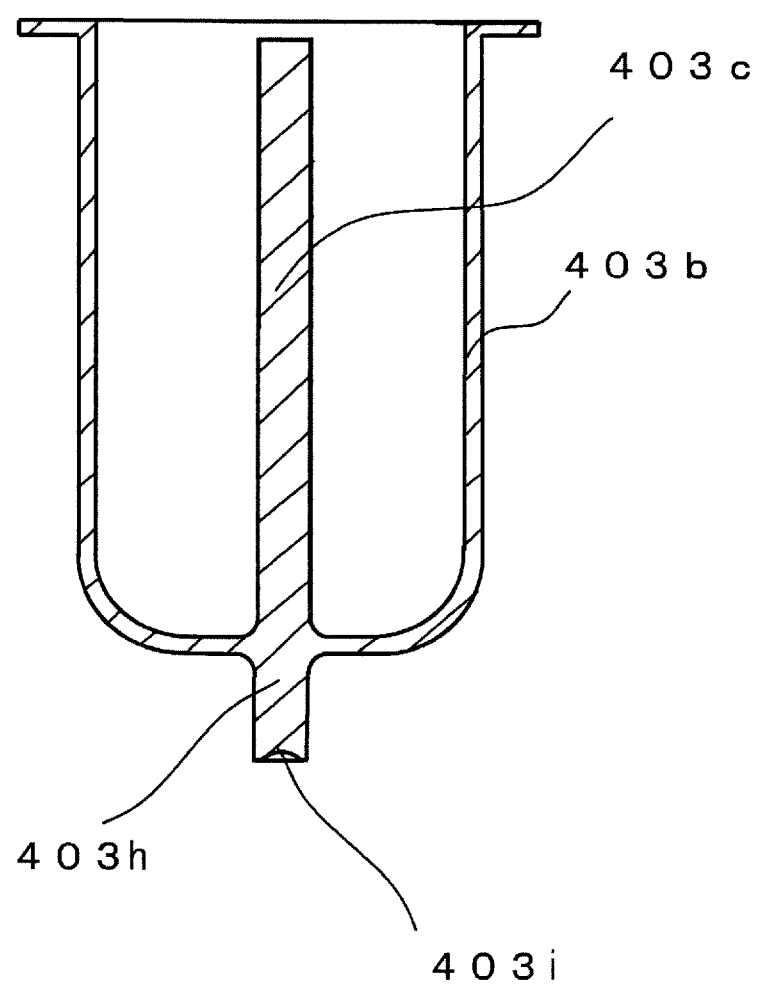
FIG. 14 is a cross-sectional view showing a modified example of a metal tip of the plastic part thermal caulking device according to the fourth embodiment of the present invention.

In thermal caulking of precision plastic parts, the diameter of the boss (boss diameter) can be 1 mm or smaller. There are cases where, even when the boss diameter is 0.5 mm, for example, a convex round head needs to be formed on the boss. In such cases, as in the modified example of the metal tip of the fourth embodiment shown in FIG. 14, thermal caulking is performed with a metal tip of which a pressing surface 403*i* of a heating rod leading end 403*h* is an upwardly convex curved shape.

Fifth Embodiment

For the first embodiment to the fourth embodiment, the examples in which thermal caulking is performed with one metal tip have been described. As a fifth embodiment, an example in which two metal tips are disposed face to face and an object to be thermally caulked is thermally caulked while being clamped between the two metal tips will be described.

Figure 15A:
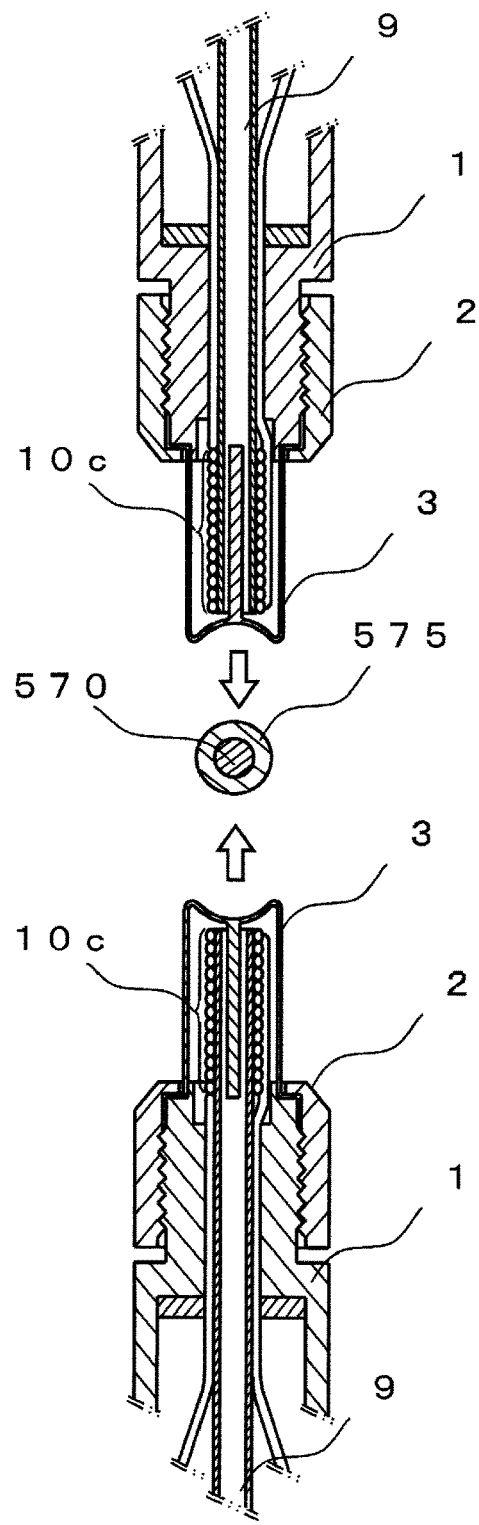
FIG. 15A is a cross-sectional view showing the major part of a caulking unit of a plastic part thermal caulking device according to a fifth embodiment of the present invention, in juxtaposition with an object to be caulked.
Figure 15B:
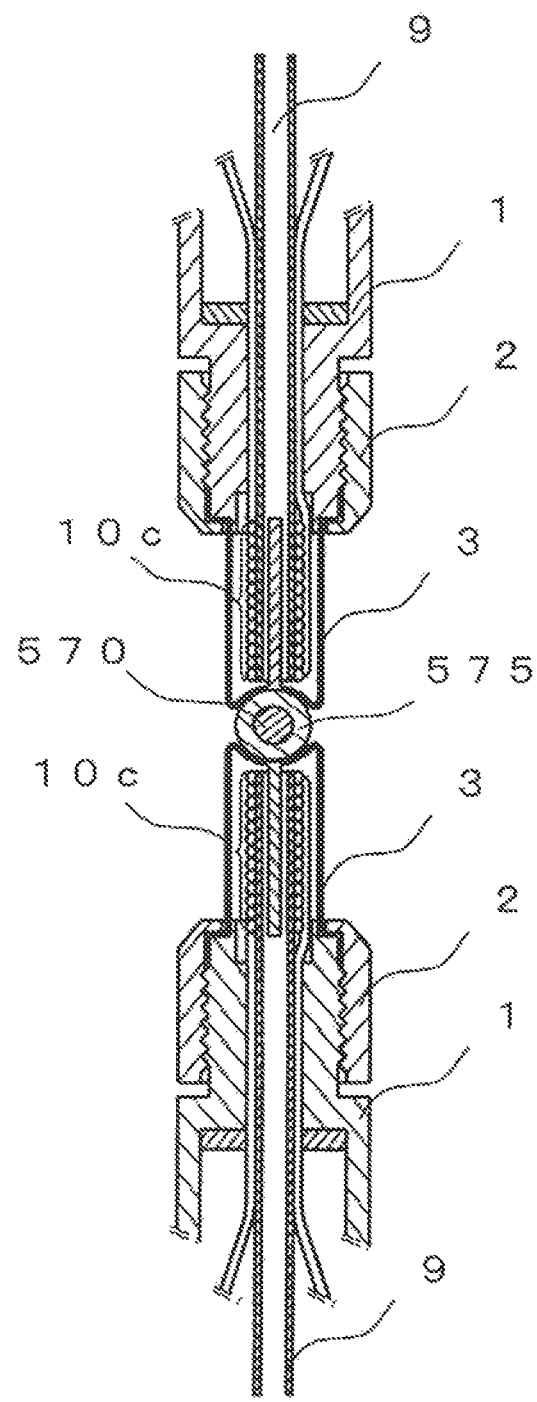
FIG. 15B is a cross-sectional view showing the major part of the caulking unit of the plastic part thermal caulking device according to the fifth embodiment of the present invention, in juxtaposition with the object to be caulked.
Figure 16:
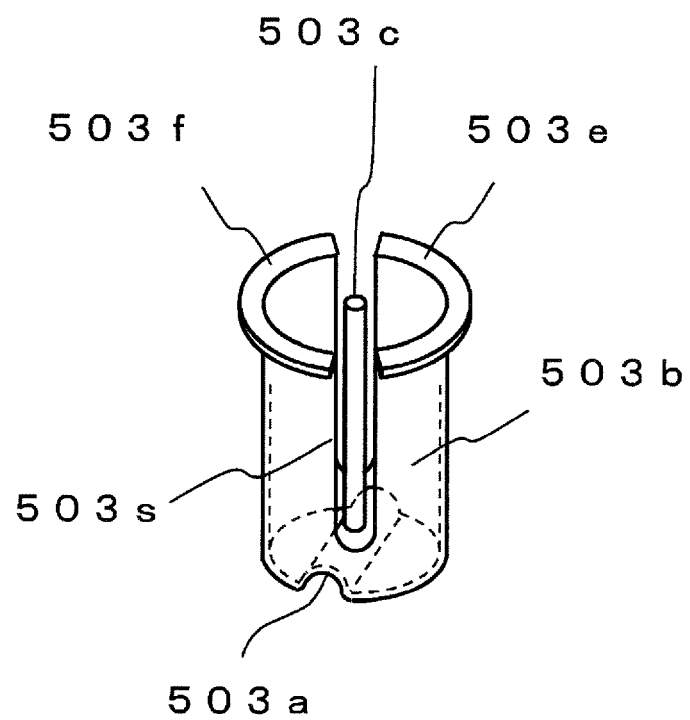
FIG. 16 is an external perspective view of a metal tip of the plastic part thermal caulking device according to the fifth embodiment of the present invention.

FIG. 15A shows a state before the metal tips 3, 3 of a thermal caulking device having the same configuration as the first embodiment are moved from the upper side and the lower side as indicated by the outlined arrows to clamp a pipe-like thermal caulking member 575 which is fitted on a rod-like stent 570 like the one described with FIGS. 28A to 28C. FIG. 15B shows a state in which a high-frequency current starts to be applied to the high-frequency induction coil 10*c* while the pipe-like thermal caulking member 575 containing the rod-like stent 570 is clamped by the metal tips 3, 3. A groove having a U-shaped curved surface is formed in each of the pressing surfaces of the metal tips 3, 3. FIG. 16 is an external perspective view of a metal tip 503 as a single part in a modified example of the fifth embodiment. A groove having a U-shaped curved surface is formed in the pressing surface of a pressing part 503*a* of the metal tip 503, and a heating rod 503 is provided upright at the center on the inner side of the U-shaped curved surface. In the case where the rod-like stent 570 is thin and the thermal caulking member is small, a metal tip having more suitable dimensions and shape can be used instead of the metal tip shown in FIGS. 15A and 15B.

As shown in FIG. 15B, when a high-frequency current is applied to the high-frequency induction coil 10*c*, each of the heating rods 3*c* generates heat, and the heat of the heating rods 3*c* transfers to the pressing part 3*a* having a U-shaped curved surface, so that the thermal caulking member 575 and the stent 570 clamped by the pair of metal tips 3, 3 generate heat and are thermally caulked.

Such a form of thermal caulking has an effect that it is possible to stably and precisely thermally caulk small plastic parts under the best thermal caulking conditions stored in advance, by applying the thermal caulking device of this embodiment to thermal caulking of the stent shown in FIG. 28 or to thermal caulking of the leading end part of the endoscope shown in FIG. 29 which have been described as the conventional examples.

Sixth Embodiment

For the first embodiment to the fifth embodiment, the examples in which high-frequency induction heating means is used as metal tip heating means have been described, but the heating means may be electrical heating means. In the sixth embodiment, an example in which electrical heating means is used as the heating means will be described.

Figure 22:
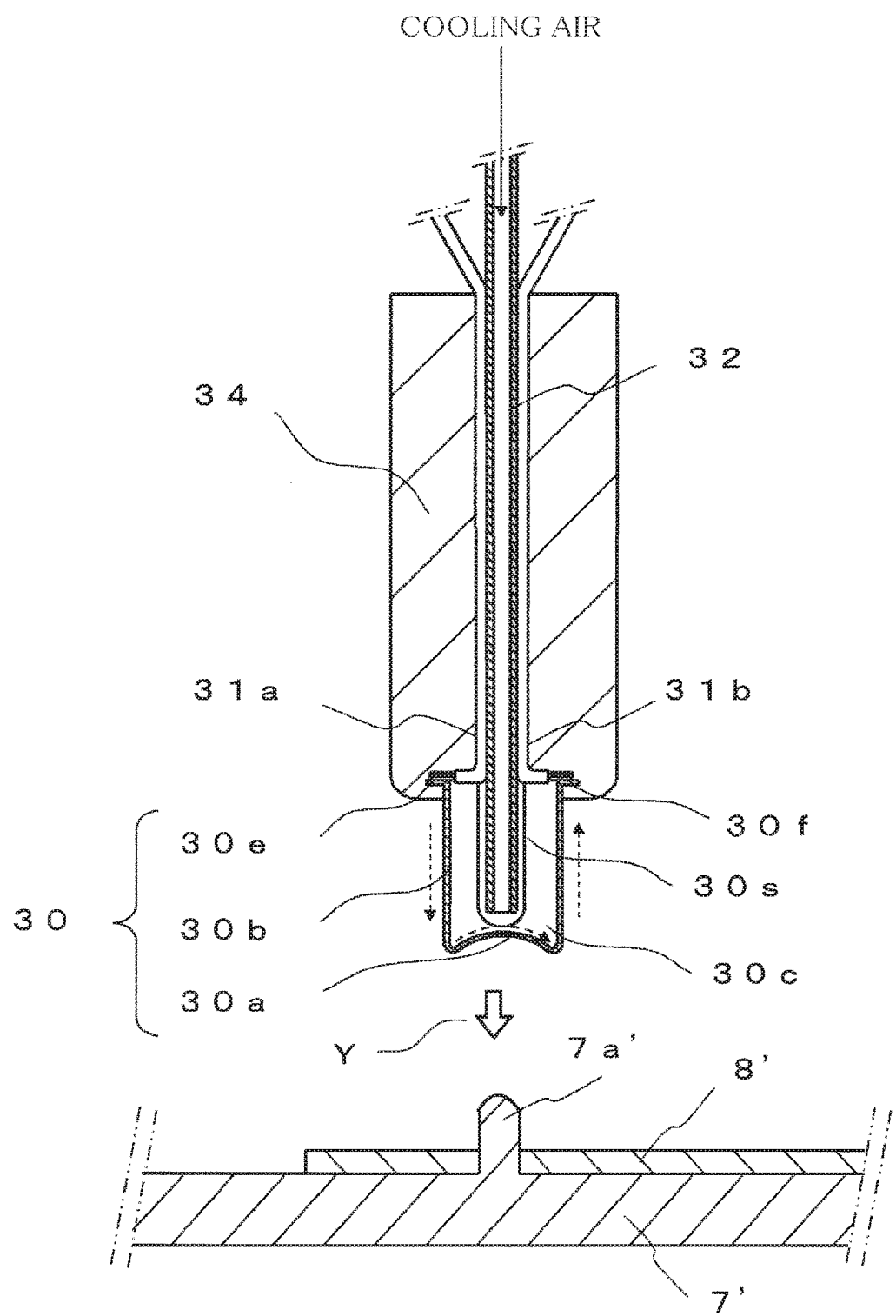
FIG. 22 is a cross-sectional view showing the major part of a caulking unit of a first conventional plastic part thermal caulking device, in juxtaposition with an object to be caulked.

In the conventional caulking device described with FIG. 22, the lead wires 31*a*, 31*b* are electrically connected to the flanges 30*e*, 30*f*, respectively, of the metal tip 30 by welding or screwing fixation, and a current is applied from one lead wire 31*a* to the other lead wire 31*b* to generate heat by Joule heating.

Figure 17:
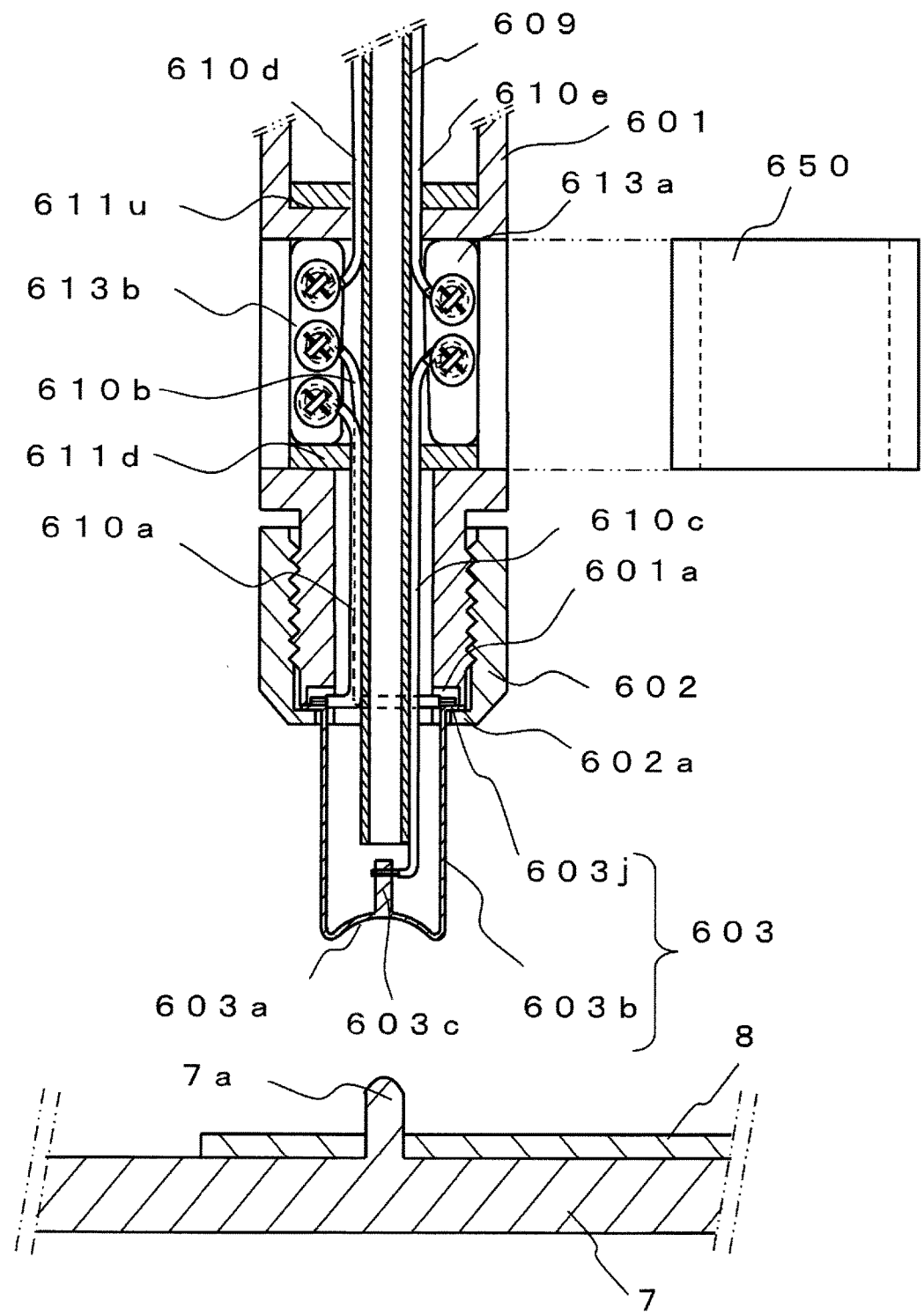
FIG. 17 is a cross-sectional view showing the major part of a caulking unit of a plastic part thermal caulking device according to a sixth embodiment of the present invention, in juxtaposition with an object to be caulked.
Figure 18:
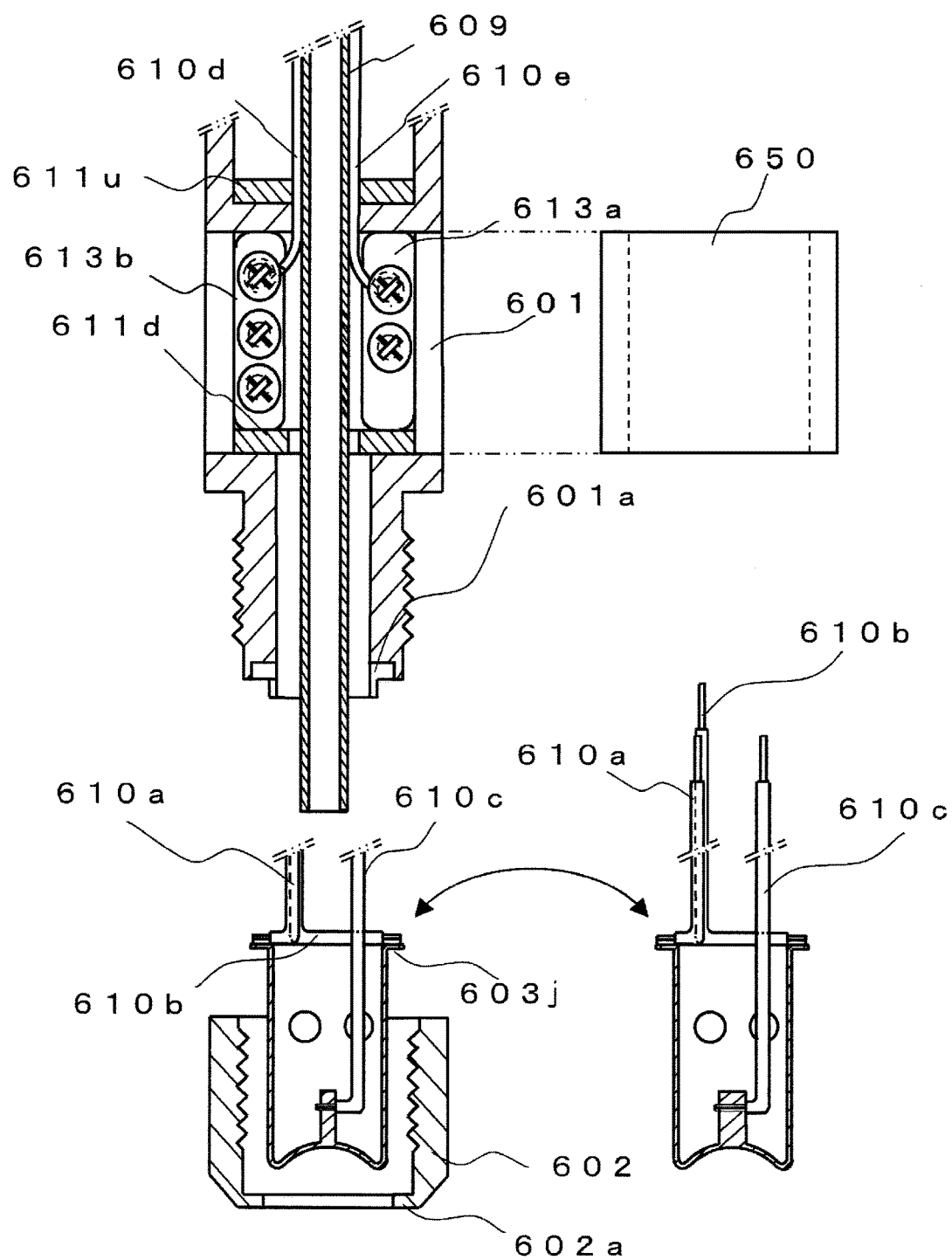
FIG. 18 is a view showing an exploded cross-sectional view of the caulking unit of the plastic part thermal caulking device according to the sixth embodiment of the present invention, along with a cross-sectional view of a replacement metal tip.
Figure 19A:
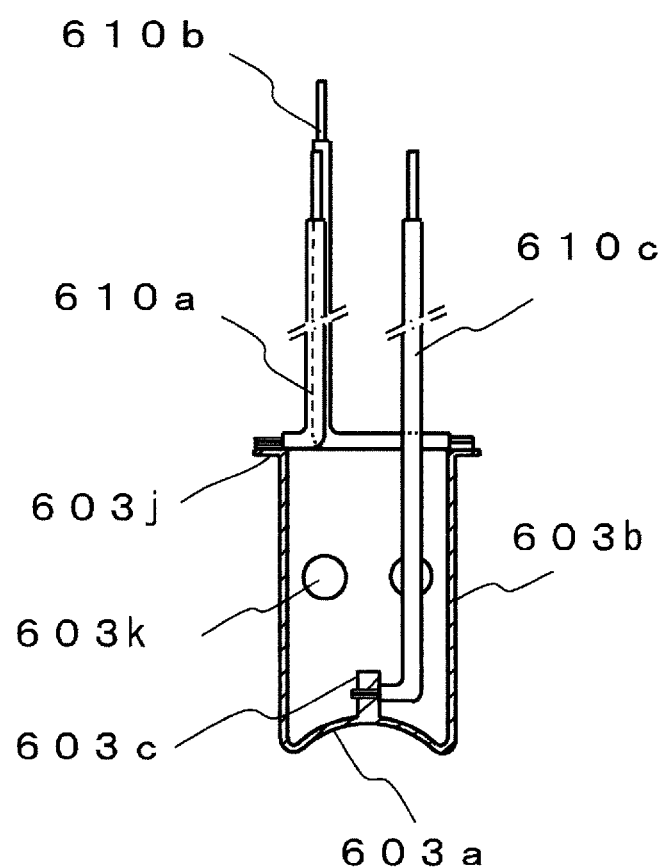
FIG. 19A is a cross-sectional view in which lead wires are connected to a metal tip of the plastic part thermal caulking device according to the sixth embodiment of the present invention.
Figure 19B:
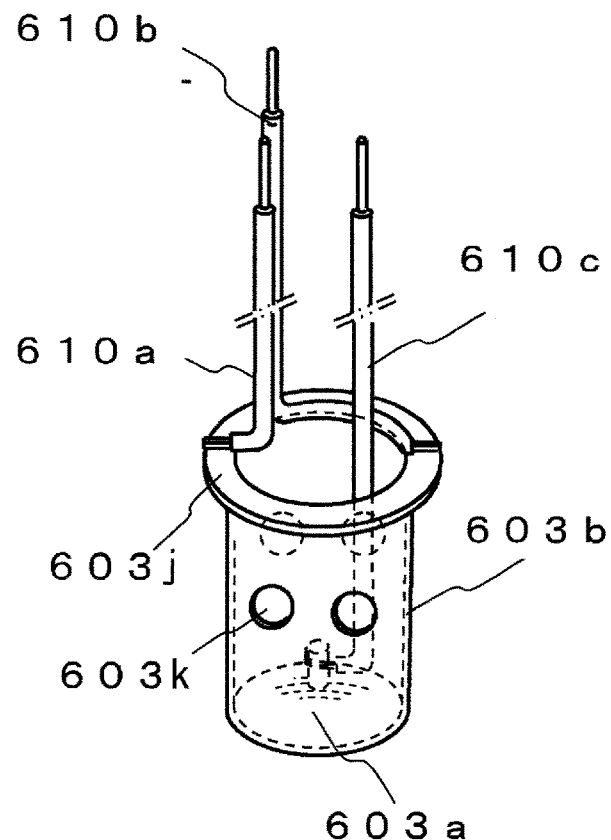
FIG. 19B is an external perspective view in which the lead wires are connected to the metal tip of the plastic part thermal caulking device according to the sixth embodiment of the present invention.

In the sixth embodiment, as shown in FIG. 17, FIG. 18, and FIG. 19 which show the outlines of the major part of the caulking unit and the metal tip, lead wires 610*a*, 610*b* and a lead wire 610*c* are respectively electrically connected by welding or screw fixation to a flange 603*j* of a metal tip 603 and a heating rod 603*c* provided upright at the center of a pressing part 603*a* of the metal tip 603. In particular, as can be seen from FIG. 19B, the two lead wires 610*a*, 610*b* are connected at positions facing each other in the flange 603*j* of the metal tip, and the other lead wire 610*c* is connected to the heating rod 603*c*. A current flows from the lead wire 610*c* connected to the heating rod 603*c* to the lead wires 610*a*, 610*b* connected to the flange 603*j*.

As shown in FIG. 17, the lead wires 610*a*, 610*b*, 610*c* have predetermined lengths, and have one ends connected to the metal tip 603 and the other ends screw-fixed on terminal strips 613*a*, 613*b* disposed inside the cavity of a holder 601. Lead wires 610*d*, 610*e* connected to a power source (not shown) are screw-fixed on the terminal strips 613*a*, 613*b* disposed inside the cavity of the holder 601.

Figure 19C:
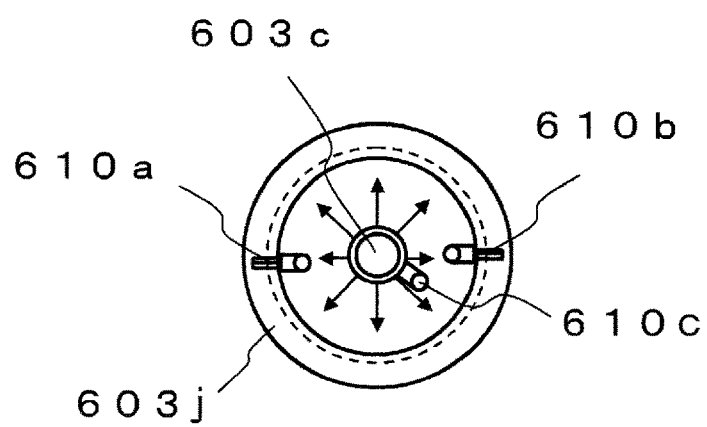
FIG. 19C is a plan view of the metal tip of the plastic part thermal caulking device according to the sixth embodiment of the present invention.

When a current is applied from the power source (not shown) through the one lead wire 610*e*, the terminal strip 613*a*, and the lead wire 610*c* to the heating rod 603*c*, the heating rod 603*c* first generates heat by being supplied with the current. Then, the current flows from the heating rod 603*c* through the pressing part 603*a*, the wall part 603*b*, and the flange 603*j* to the two lead wires 610*a*, 610*b*, and flows through the terminal strip 613*b* to 610*d*. Thus, the center of the pressing part 603*a* where the heating rod 603*c* is located reaches a high temperature, and the heat diffuses from the center toward the outer periphery of the pressing part 603*a* as shown in FIG. 19C.

As shown in FIG. 17 and FIG. 18, in the position of the holder 601 where the terminal strips 613*a*, 613*b* are provided, the outer periphery of the holder 601 is cut out, and a lid 650 is provided so as to close this cutout portion. The lid 650 is removable so that the lead wires 610*a*, 610*b*, 610*c* can be attached to or removed from the terminal strips 613*a*, 613*b* disposed inside the cavity of the holder 601.

FIG. 17 is a configurational view showing a plastic part thermal caulking device according to the sixth embodiment of the present invention. FIG. 17 shows the major part of the thermal caulking unit of the thermal caulking device, the plastic part 7 with the protruding boss 7*a*, and the metal plate 8 laid on the plastic part 7 with the boss 7*a* passing through the hole of the metal plate 8.

FIG. 18 is an exploded cross-sectional view of the plastic part thermal caulking device according to the sixth embodiment of the present invention in which the screw of a holder cap 602 is loosened and the holder cap 602 is removed from the holder 601. In the sixth embodiment, the holder 601 and the holder cap 602 are screw-connected to each other to hold the metal tip 603. Since the metal tip is not molded with a resin materiel as in the conventional example, the device can be used with another metal tip replacing the metal tip.

In the sixth embodiment of the present invention, when replacing the metal tip, it is necessary to remove the lid 650 of the holder 601, loosen the screws fixed on the terminal strips 613*a*, 613*b* inside the holder 601 with a driver, and remove the lead wires 610*a*, 610*b*, 610*c* on the metal tip side. Alternatively, the lid 650 covering the terminal strips 613*a*, 613*b* of the lead wires 610*a*, 610*b*, 610*c* may be removed from the holder 601 first, and then the lead wires 610*a*, 610*b*, 610*c* on the metal tip side may be removed with a driver, or the lid 650 may be removed from the holder 601 first after the screw of the holder cap 602 is loosened, and then the lead wires 610*a*, 610*b*, 610*c* on the metal tip side may be removed with a driver. In either case, the metal tip 603 can be replaced with another metal tip. FIG. 18 is a cross-sectional view of a metal tip shown as another metal tip of which the heating rod has a larger diameter, with the arrow indicating replaceability.

FIG. 19A is a cross-sectional view showing the metal tip 603 with the lead wires 610a, 610b, 610c connected thereto; FIG. 19B is an external perspective view of the metal tip 603; and FIG. 19C is a plan view of the metal tip 603. In the metal tip 603, a wall part 603b rises from around the pressing part 603a having an upwardly convex spherical surface, and the flange 603j is formed at the upper end of the wall part 603b. A plurality of open holes 603k are formed in the wall part 603b through which the cavity inside the metal tip 603 and the outside of the metal tip 603 communicate with each other. The perspective view of FIG. 19B shows that four open holes 603k are bored in the well part 603b. The lead wires 610a, 610b are connected to the flange 603j, while the other lead wire 610c is connected to the heating rod 603c provided upright at the center of the pressing part 603a.

The arrows in FIG. 19C show an image that the center of the pressing part where the heating rod 603c is located reaches a high temperature and heat diffuses from the center toward the outer periphery.

It is the same as with the metal tips shown in the first embodiment to the fifth embodiment that the metal tip 603 has the cavity inside through which a cooling fluid flows, the open holes through which the cooling fluid is discharged outside, and the heating rod 603c provided at the center of the pressing part 603a. However, in the sixth embodiment, electrical power is supplied first to the heating rod 603c located at the center and a current is passed to the periphery of the pressing part 603a like an earth.

In the above description, the example in which the one lead wire 610c is connected to the heating rod 603c and the two lead wires 610a, 610b are connected to the positions facing each other in the flange 603j has been shown. It is in order to cause a current to flow radially from the one lead wire 610c connected to the heating rod 603c that the two lead wires 610a, 610b are connected to the positions facing each other in the flange 603j. The number of the lead wires connected to positions facing each other in the flange 603j should be at least two, and may be three or four, if the space permits.

Since the metal tip 603 generates heat by being supplied with a current, the center of the pressing part 603a where the heating rod 603c, which is supplied with electrical power first, is located reaches a high temperature, and heat diffuses from the center toward the outer periphery. When pressed with the metal tip 603, the boss 7a is melted by the heat transferring thereto from the pressing part 603a. As cooling air is sprayed from the cooling pipe 609 toward the heating rod 603c and the pressing part 603a, the heating rod 603c and the pressing part 603a are cooled. The heat taken away from the heating rod 602c is discharged through the open holes 603k to the outside of the metal tip 603.

Thus, it is the same as in the first embodiment to the fifth embodiment that pressing part 603a is heated from the center, where the heating rod 603c of the metal tip 603 in the sixth embodiment is located, toward the periphery, and that the pressing part 603a is cooled from the center toward the periphery. In this way, thermal caulking is performed by rapidly heating and rapidly cooling the boss 7a etc. in this embodiment. That current application conditions and pressing conditions are stored in advance and that optimal conditions are read out to perform thermal caulking work are the same as in the first embodiment to the fifth embodiment, and therefore the description thereof will be omitted here.

As in the other embodiments, the metal tip 603 is structured to be clamped by the holder and the holder cap made of an insulating material such as plastic or wood.

Seventh Embodiment

A plastic part thermal caulking device according to a seventh embodiment of the present invention has sheet metals 740, 741 having spring properties instead of the lead wires 610a, 610b, 610c of the sixth embodiment. That is, while in the sixth embodiment the metal tip 603 with the lead wires 610a, 610b, 610c joined thereto in advance is replaceable, in the seventh embodiment, instead of the lead wires 610a, 610b, 610c, the sheet metals 740, 741 having spring properties are incorporated into a holder 701 so that a metal tip 703 can be replaced alone.

Figure 20:
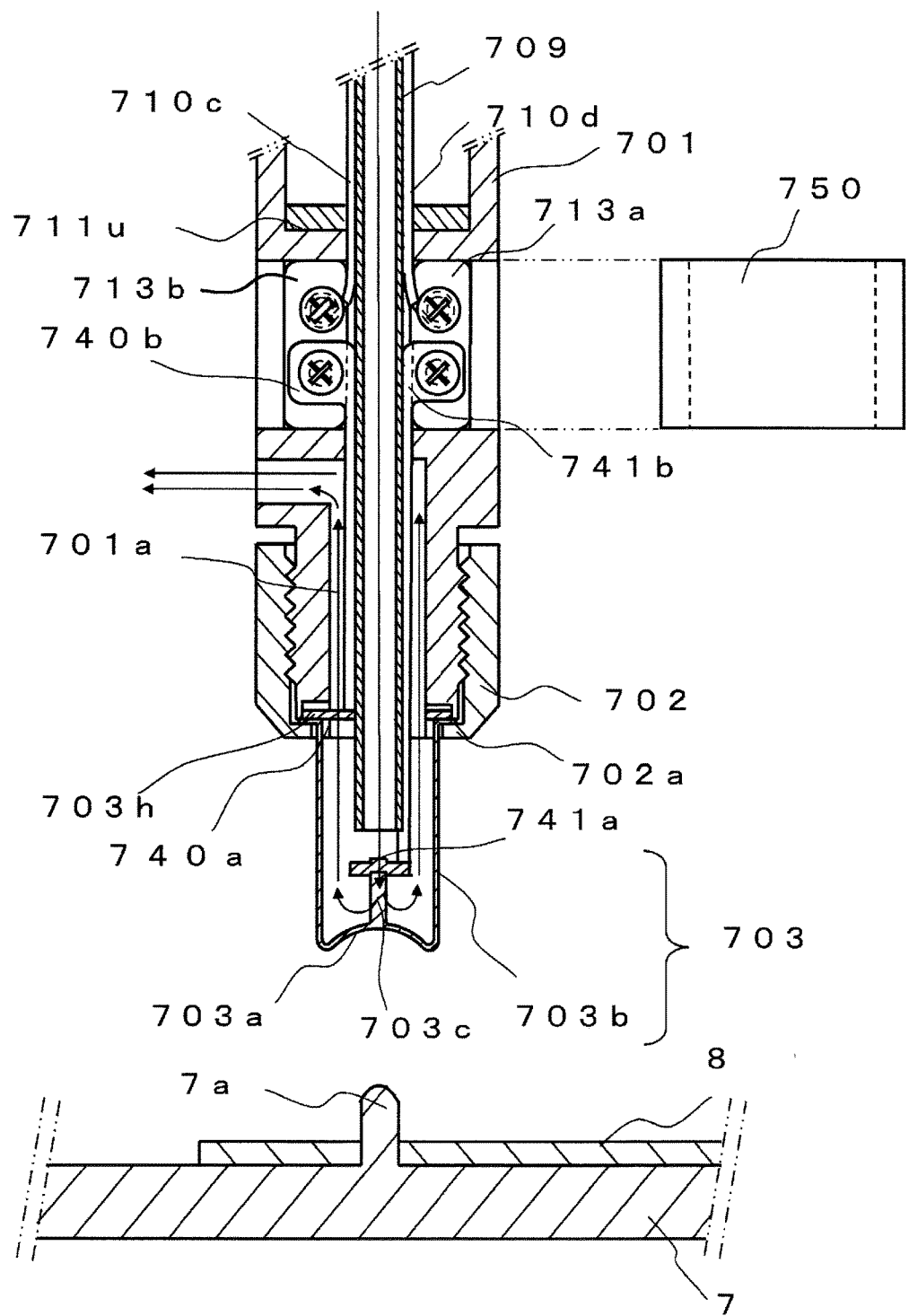
FIG. 20 is a cross-sectional view showing the major part of a caulking unit of a plastic part thermal caulking device according to a seventh embodiment of the present invention, in juxtaposition with an object to be caulked.

FIG. 20 is a configurational view showing the plastic part thermal caulking device according to the seventh embodiment of the present invention. FIG. 20 shows the major part of a thermal caulking unit of the thermal caulking device, the plastic part 7 with the protruding boss 7a, and the metal plate 8 laid on the plastic part 7 with the boss 7a passing through the hole of the metal plate 8.

In the seventh embodiment of the present invention, as in the third embodiment already described, a heat discharge hole 701a is formed in the holder 701 so that heat is discharged along with a cooling fluid through the heat discharge hole 701a of the holder 701. Thus, the mechanical strength of the metal tip is increased by not providing an opening, such as a slit, in a wall part 703b of the metal tip. As a result, it is allowed to press hard the leading end of the boss 7a with a pressing part 703a of the thin metal tip.

Figure 21:
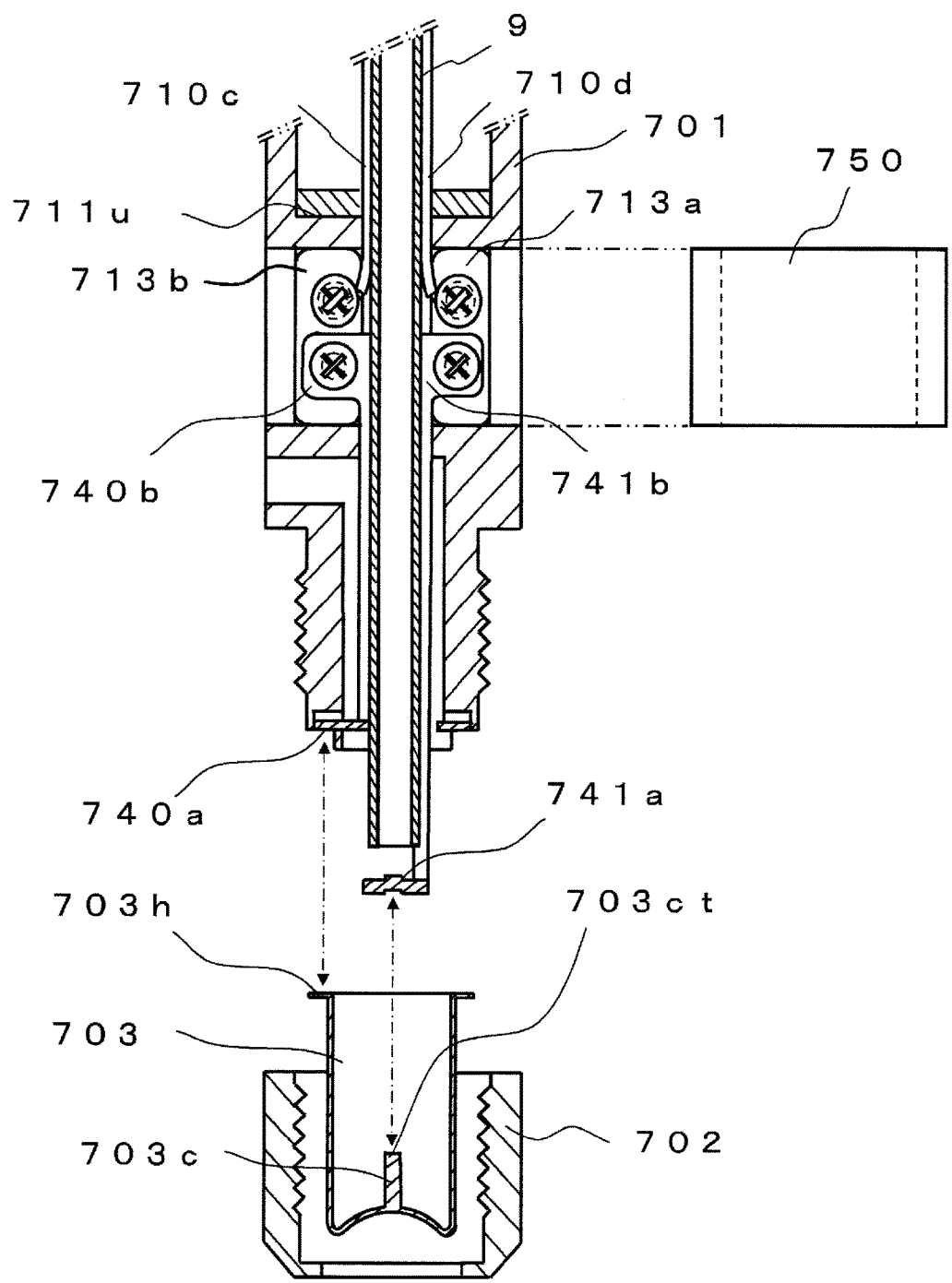
FIG. 21 is an exploded cross-sectional view of the caulking unit of the plastic part thermal caulking device according to the seventh embodiment of the present invention.

FIG. 21 is an exploded cross-sectional view of the plastic part thermal caulking device according to the seventh embodiment of the present invention in which the screw of a holder cap 702 is loosened and the holder cap 702 is removed from the holder 701. The sheet metals 740, 741 having spring properties are screw-fixed at their upper ends 740b, 741b to terminal strips 713a, 713b inside the holder 701. Therefore, when the screw of the holder cap 702 is loosened and the holder cap 702 is removed from the holder 701, the metal tip 703, which has been pressed against the sheet metals 740, 741, is separated from the sheet metals 740, 741 and removed along with the holder cap 702 from the holder 701. As necessary, the metal tip 703 can be replaced with another metal tip in the state of FIG. 21.

According to the seventh embodiment of the present invention, it is convenient in that lead wires 710a, 710b need not be connected in advance to the metal tip 703 end that only the metal tip needs to be replaced.

Aspects of the Present Invention

A first aspect of the present invention is a thermal caulking device which caulks a portion of a plastic part as an object to be caulked, the thermal caulking device including: a metal tip having a pressing part which presses the object to be caulked, a heating rod which is provided upright at a center part of the pressing part, and a wall part which is provided upright on the outer periphery of the pressing part; heating means for heating the heating rod; a cooling pipe which cools the heating rod; cooling fluid supply means for supplying a cooling fluid to the cooling pipe; a holder which holds the metal tip and the cooling pipe so that the cooling pipe delivers the cooling fluid toward the heating rod; and control means for controlling the heating means and the cooling fluid supply means, wherein the control means heats the pressing part from the heating rod by the heating means, and after the object to be caulked is thermally caulked by the pressing part, supplies the cooling fluid from the cooling fluid supply means to the cooling pipe to cool the pressing part from the heating rod.

A second aspect of the present invention is the thermal caulking device according to the first aspect, wherein the holder holds the metal tip and the cooling pipe so that a leading end portion of the cooling pipe covers the outer peripheral surface of the heating rod of the metal tip with a clearance therebetween; the heating means has a coil which is provided on the inside of the wall part of the metal tip and wound on the outer peripheral surface of the leading end portion of the cooling pipe, and a power source which supplies a high-frequency current to the coil; and the control means applies a high-frequency current from the power source to the coil, and heats the pressing part from the heating rod by high-frequency induction heating through the coil.

A third aspect of the present invention is the thermal caulking device according to the first aspect, wherein the heating means has two or more current-carrying members of which one is connected to the leading end of the heating rod and the other is connected to the leading end of the wall part, and a power source which supplies electrical power to the current-carrying members; and the control means applies a current from the power source through the current-carrying members to the heating rod, and heats the metal tip from the heating rod by electrical heating.

A fourth aspect of the present invention is the thermal caulking device according to any one of the first to third aspects, wherein an opening is formed in the wall part.

A fifth aspect of the present invention is the thermal caulking device according to any one of the first to third aspects, wherein an open hole through which a cavity formed by the wall part of the metal tip and the outside of the holder communicate with each other is formed in a leading end part of the holder.

A sixth aspect of the present invention is the thermal caulking device according to any one of the first to fifth aspects, further including storage means for storing thermal caulking conditions including at least values related to the heating means and values related to the flow rate of the cooling fluid, wherein the control means reads out one or more thermal caulking conditions stored in the storage means, and controls the cooling fluid supply means and the heating means according to the thermal caulking conditions having been read out.

A seventh aspect of the present invention is the thermal caulking device according to any one of the first to third aspects wherein the metal tip has a flange formed at the leading end of the wall part; and the holder is provided with a removable holder cap which, together with a leading end part of the holder, clamps the flange of the metal tip.

An eighth aspect of the present invention is the thermal caulking device according to any one of the first to seventh aspects, wherein the pressing surface of the pressing part has a spherical shape concave in the pressing direction.

A ninth aspect of the present invention is the thermal caulking device according to any one of the first to seventh aspects, wherein the pressing surface of the pressing part has a U-groove shape concave in the pressing direction.

A tenth aspect of the present invention is the thermal caulking device according to any one of the first to seventh aspects, wherein the pressing part uses, as the pressing surface, a heating rod leading end protruding from the heating rod in the pressing direction.

An eleventh aspect of the present invention is the thermal caulking device according to any one of the first to tenth aspects, wherein the cooling fluid is air and the cooling fluid supply means is a blower.

A twelfth aspect of the present invention is the thermal caulking device according to any one of the first to eleventh aspects, further including pressing operation means which can support the holder and move the holder in the pressing direction.

A thirteenth aspect of the present invention is the thermal caulking device according to any one of the first to twelfth aspects, wherein the holder is provided with a spring which urges the holder in the pressing direction, and the object to be caulked is pressed by the urging force of the spring.

A fourteenth aspect of the present invention is the thermal caulking device according to any one of the first to thirteenth aspects, wherein the heating means has a coil which is provided on the inside of the wall part of the metal tip and wound around the heating rod, and a power source which supplies a high-frequency current to the coil, and the high-frequency current is supplied from the power source to the coil to heat the heating rod by high-frequency induction heating through the coil.

INDUSTRIAL APPLICABILITY

The present invention can be widely applied to common plastic part thermal caulking devices, as well as to thermal caulking devices intended, for example, for catheter tubes or other small precision plastic parts.

EXPLANATION OF REFERENCE SIGNS

1 Holder
2 Holder cap
3 Metal tip
3a Pressing part
3b Wall part
3c Heating rod
3e, 3f Flange
3s Slit
7 Plastic part
7a Boss of the plastic part
8 Metal plate
9 Cooling pipe
10, 10a, 10b Lead Wire
10c High-frequency induction coil

The invention claimed is:
1. A thermal caulking device which caulks a portion of a plastic part as an object to be caulked, the thermal caulking device comprising:
   a metal tip having a pressing part which presses the object to be caulked, a heating rod which is provided upright at a center part of the pressing part, and a wall part which is provided upright on the outer periphery of the pressing part;
   heater for heating the heating rod;
   a cooling pipe which cools the heating rod;
   cooling fluid supplier for supplying a cooling fluid to the cooling pipe;
   a holder which holds the metal tip and the cooling pipe so that the cooling pipe delivers the cooling fluid toward the heating rod; and
   controller for controlling the heater and the cooling fluid supplier, wherein the controller heats the pressing part from the heating rod by the heater, and after the object to be caulked is thermally caulked by the pressing part, supplies the cooling fluid from the cooling fluid supplier to the cooling pipe to cool the pressing part from the heating rod.

2. The thermal caulking device according to claim 1, wherein
the holder holds the metal tip and the cooling pipe so that a leading end portion of the cooling pipe covers the outer peripheral surface of the heating rod of the metal tip with a clearance therebetween,
heater has a coil which is provided on the inside of the wall part of the metal tip and wound on the outer peripheral surface of the leading end portion of the cooling pipe, and a power source which supplies a high-frequency current to the coil, and
the controller applies a high-frequency current from the power source to the coil, and heats the pressing part from the heating rod by high-frequency induction heating through the coil.

3. The thermal caulking device according to claim 1, wherein
the heater has at least two current-carrying members of which one is connected to a leading end of the heating rod and a remaining of the at least two current-carrying members, excluding the one that is connected to the leading end of the heating rod, is connected to the leading end of the wall part, and a power source which supplies electrical power to the current-carrying members, and
the controller applies a current from the power source through the current-carrying members to the heating rod, and heats the pressing part from the heating rod by electrical heating.

4. The thermal caulking device according to claim 1, wherein an opening is formed in the wall part.

5. The thermal caulking device according to claim 1, wherein an open hole through which a cavity formed by the wall part of the metal tip and the outside of the holder communicate with each other is formed in a leading end part of the holder.

6. The thermal caulking device according to claim 1, further comprising a storage part for storing thermal caulking conditions including at least values related to the heater and values related to the flow rate of the cooling fluid, wherein
the controller reads out one or more thermal caulking conditions stored in the storage part and controls the cooling fluid supplier and the heater according to the thermal caulking conditions having been read out.

7. The thermal caulking device according to claim 1, wherein
the metal tip has a flange formed at the leading end of the wall part, and
the holder is provided with a removable holder cap which, together with a leading end part of the holder, clamps the flange of the metal tip.

8. The thermal caulking device according to claim 1, wherein the pressing surface of the pressing part has a spherical shape concave in the pressing direction.

9. The thermal caulking device according to claim 1, wherein the pressing surface of the pressing part has a U-groove shape concave in the pressing direction.

10. The thermal caulking device according to claim 1, wherein the pressing part uses, as the pressing surface, a heating rod leading end protruding from the heating rod in the pressing direction.

11. The thermal caulking device according to claim 1, wherein the cooling fluid is air and the cooling fluid supplier is a blower.

12. The thermal caulking device according to claim 1, further comprising pressing operator which can support the holder and move the holder in the pressing direction.

13. The thermal caulking device according to claim 1, wherein the holder is provided with a spring which urges the holder in the pressing direction, and the object to be caulked is pressed by the urging force of the spring.

14. The thermal caulking device according to claim 1, wherein
the heater has a coil which is provided on the inside of the wall part of the metal tip and wound around the heating rod, and a power source which supplies a high-frequency current to the coil, and
the high-frequency current is supplied from the power source to the coil to heat the heating rod by high-frequency induction heating through the coil.

* * * * *